United States Patent
Igarashi

(10) Patent No.: US 11,590,273 B2
(45) Date of Patent: Feb. 28, 2023

(54) BIOLOGICAL COMPONENT COLLECTION SYSTEM WITH PRESSURE CONTROLLED FILTER AND METHOD

(71) Applicant: TERUMO KABUSHIKI KAISHA, Shibuya-ku (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 314 days.

(21) Appl. No.: 16/650,747

(22) PCT Filed: Sep. 27, 2018

(86) PCT No.: PCT/JP2018/035875
§ 371 (c)(1),
(2) Date: Mar. 25, 2020

(87) PCT Pub. No.: WO2019/065813
PCT Pub. Date: Apr. 4, 2019

(65) Prior Publication Data
US 2020/0306442 A1    Oct. 1, 2020

(30) Foreign Application Priority Data
Sep. 28, 2017 (JP) .............................. JP2017-187971

(51) Int. Cl.
*A61M 1/36* (2006.01)
*A61M 1/02* (2006.01)
*A61M 1/38* (2006.01)
*A61M 1/30* (2006.01)

(52) U.S. Cl.
CPC ........ *A61M 1/3693* (2013.01); *A61M 1/0218* (2014.02); *A61M 1/305* (2014.02); *A61M 1/3627* (2013.01); *A61M 1/382* (2013.01); *A61M 2202/0014* (2013.01); *A61M 2202/0415* (2013.01); *A61M 2205/125* (2013.01); *A61M 2205/7545* (2013.01)

(58) Field of Classification Search
CPC .. A61M 1/0218; A61M 1/305; A61M 1/3627; A61M 1/3693; A61M 1/382; A61M 2202/0014; A61M 2202/0415; A61M 2205/125; A61M 2205/7545
See application file for complete search history.

(56) References Cited

U.S. PATENT DOCUMENTS 6,284,142 B1    9/2001 Muller

FOREIGN PATENT DOCUMENTS

EP    0112152 A3    6/1984
WO    2017142003 A1    8/2017

*Primary Examiner* — Dirk R Bass
(74) *Attorney, Agent, or Firm* — Sheridan Ross P.C.

(57) ABSTRACT

A centrifugal separation device of a blood component collection system, which is one form of a biological component collection system, performs a pressure release step of stopping a collection and returning pump at the end of a returning operation, and releasing a positive pressure inside a filter structural member, a clamp closure step of closing an inlet flow passage and an outlet flow passage of the filter structural member, and a collection operation starting step of starting a subsequent collection operation.

20 Claims, 17 Drawing Sheets

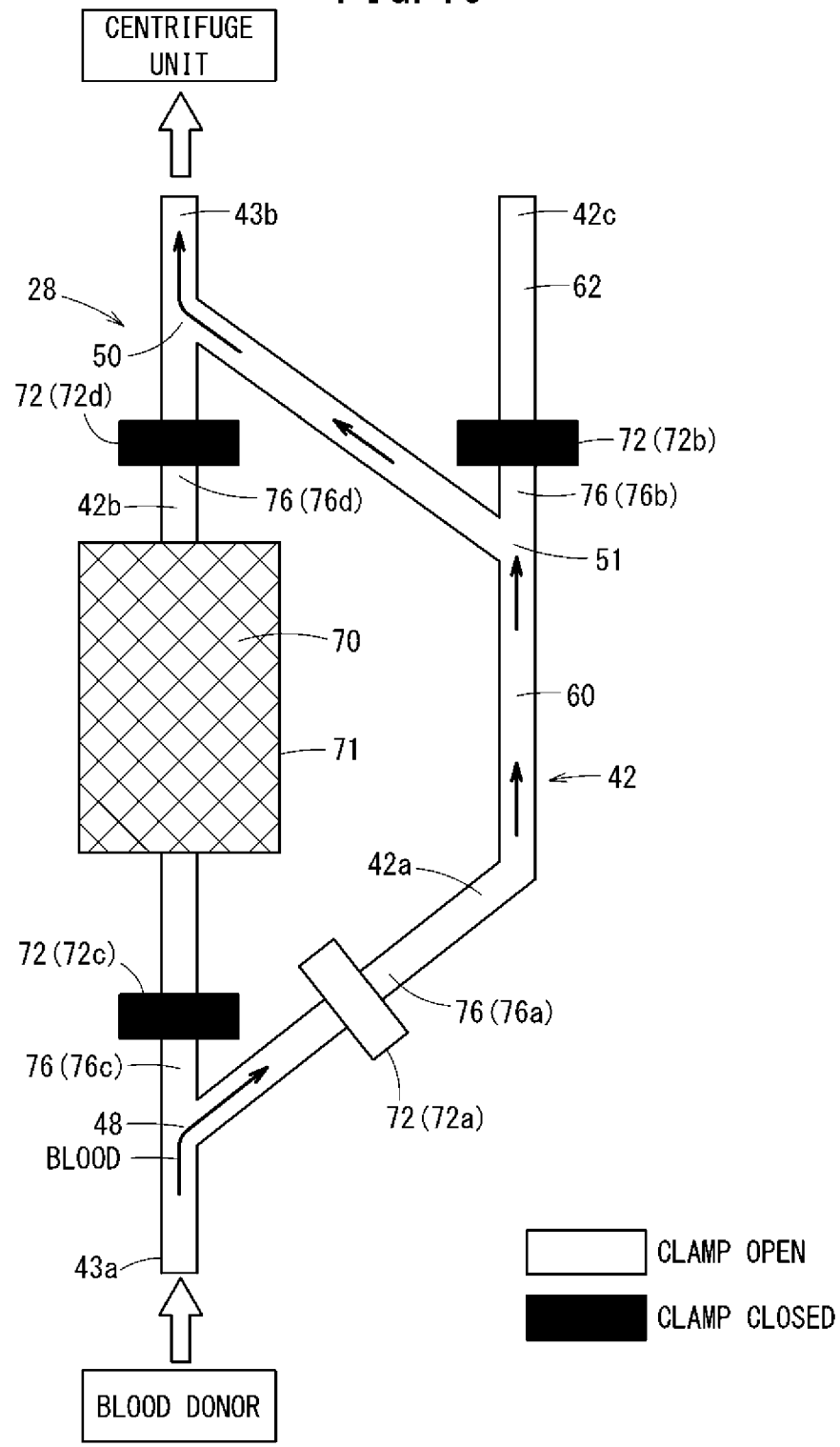

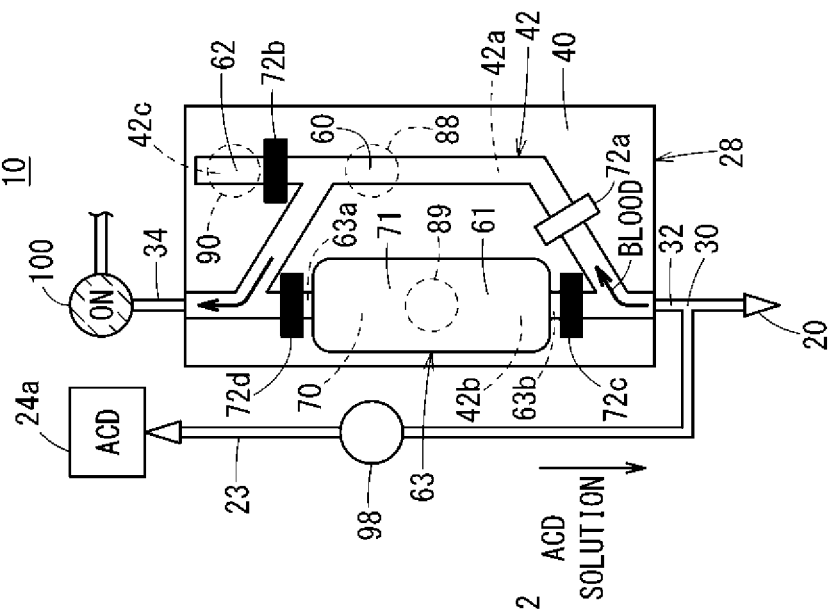
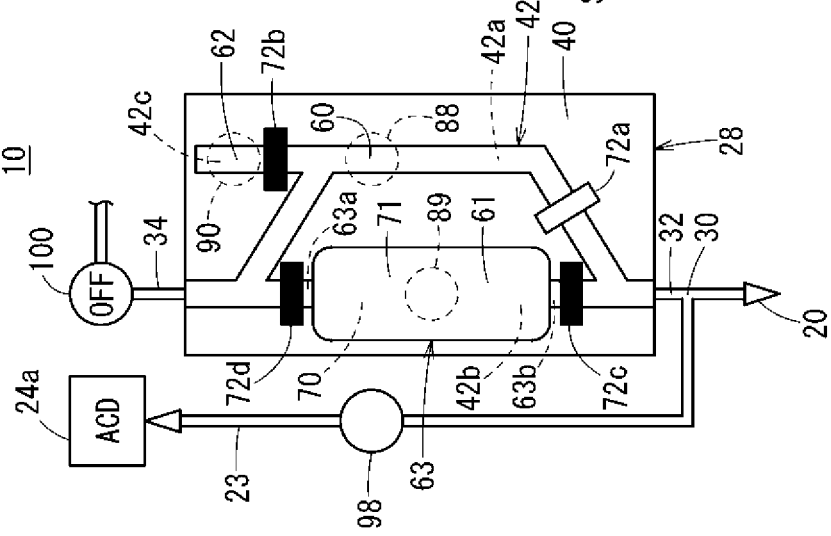
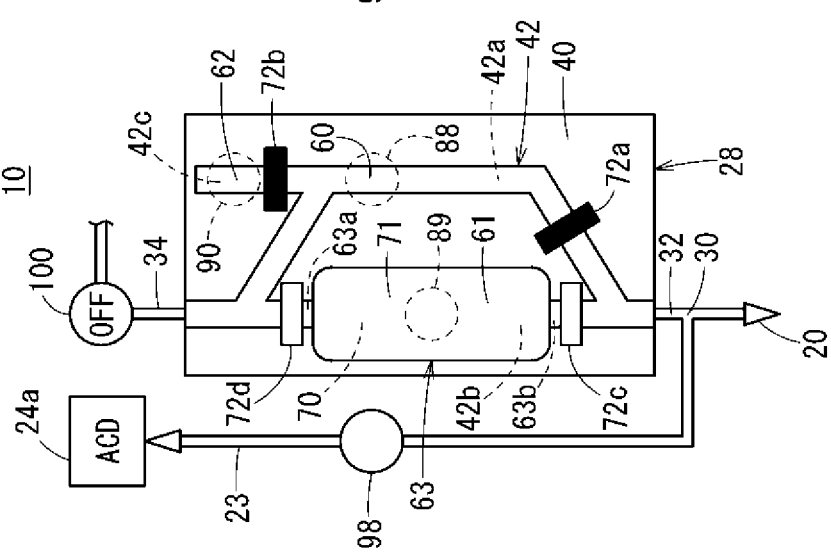

BIOLOGICAL COMPONENT COLLECTION SYSTEM WITH PRESSURE CONTROLLED FILTER AND METHOD

TECHNICAL FIELD

The present invention relates to a biological component collection system and a method of operating such a biological component collection system.

BACKGROUND ART

In blood donation in recent years, in addition to whole blood collection in which whole blood is collected from blood donors, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining blood components are returned again into the donor's body.

For example, in Japanese Laid-Open Patent Publication No. 2013-514863 (PCT), a blood component collection system is disclosed in which blood platelets are collected by centrifugally separating whole blood that is extracted from a blood donor. Such a blood component collection system includes a blood collection circuit set, which forms a circuit through which blood or blood components to be treated flow, and a centrifugal separation device (blood component separation device) on which the blood collection circuit set is mounted.

The blood collection circuit set is equipped with a plurality of bags for accommodating a blood collection line having a blood collection needle, a band-shaped channel (separator) into which whole blood is introduced, and the blood components, etc., and a cassette connected through a plurality of tubes to the bags. A plurality of flow paths, including a collection line for introducing blood from a blood donor, and a returning line for returning uncollected blood components to the blood donor, etc., are formed in the cassette. When used, the cassette is mounted in a mounting unit disposed in the blood component separation device.

SUMMARY OF INVENTION

In the blood component collection system, a collection line and a returning line are formed in parallel in the cassette, a filter structural member is provided in the returning line, and a collection and returning pump is disposed between the cassette and a blood treatment unit (centrifugal separation unit). In the case that a configuration is adopted in which a plasma component is separated from blood collected from a blood donor, the remaining blood cell components are returned to the donor, and the collection and returning pump is driven to thereby switch alternately between the collection operation and the returning operation, the following problems tend to occur.

Clamps on an inlet side and an outlet side of the filter structural member are closed at the end of the returning operation. When the clamps are closed, the pressure inside the filter structural member is a positive pressure. Accompanying a subsequent collection operation, although the collection line becomes a negative pressure, since the inlet side and the outlet side of the filter structural member are closed by the clamps, the interior of the filter structural member is maintained at a positive pressure. In addition, when transitioning from the collection operation to a subsequent returning operation, when the clamps on the inlet side and the outlet side of the filter structural member are opened, due to the difference in pressure, a rapid flow is generated from the filter structural member toward the collection line. Consequently, there is a possibility that blood having a high blood cell concentration will flow out from the filter structural member and flow into the collection line. When blood having a high blood cell concentration flows into the collection line when transitioning from the collection operation to the subsequent returning operation, the processing efficiency of the centrifugal separation device decreases, and blood having a high blood cell concentration is returned to the blood donor. Similar problems also occur in biological component collection systems other than blood component collection systems.

The present invention has been devised taking into consideration such problems, and has the object of providing a biological component collection system and a method of operating such a biological component collection system, which are capable of preventing a high concentration of biological components from flowing into a collection line when transitioning from a collection operation to a subsequent returning operation.

In order to achieve the above-described objects, the present invention is a biological component collection system, comprising a separation device having a separation processing unit, and adapted to separate a biological component from a liquid containing at least one biological component, and a biological component collection device configured to be attachable to the separation device and having a flow path formed in the interior thereof, wherein the biological component collection device includes a collection line adapted to introduce the liquid containing at least one biological component from a donor, a returning line adapted to return an uncollected biological component to the donor, and a filter structural member provided in the returning line, the collection line and the returning line communicating with each other via a branching member, the separation device includes a collection and returning pump disposed in a line between the separation processing unit and the biological component collection device, and a clamp capable of opening and closing an inlet flow path and an outlet flow path of the filter structural member, and by driving the collection and returning pump, alternately carries out a collection operation of transferring the liquid containing at least one biological component from the donor to the separation processing unit via the collection line, and a returning operation for transferring an unnecessary biological component from the separation processing unit to the donor via the returning line, and the separation device performs a pressure release step of stopping a collection and returning pump at the end of the returning operation, and releasing a positive pressure inside the filter structural member, a clamp closure step of, after the pressure release step, closing an inlet flow passage and an outlet flow passage of the filter structural member by the clamp, and a collection operation starting step of, after the clamp closure step, starting a subsequent collection operation by driving the collection and returning pump.

According to the biological component collection system of the present invention, which is configured in the manner described above, after the positive pressure in the filter structural member is released by stopping the collection and returning pump accompanying completion of the returning operation, the inlet flow passage and the outlet flow passage of the filter structural member are closed. Therefore, the subsequent collection operation is started in a state with the differential pressure between the collection line and the returning line removed. Accordingly, when clamps on the inlet side and the outlet side of the filter structural member are opened for the purpose of the next returning operation, it is possible to prevent blood having a high blood cell concentration from flowing into the collection line. Consequently, it is possible to prevent a decrease in the processing efficiency of the separation device, together with preventing blood having a high blood cell concentration from being returned to the blood donor.

The filter structural member includes a filter member, and a filter accommodating unit in which the filter member is accommodated, and the filter accommodating unit may be made of a soft material.

In the case that the filter accommodating unit is made of a soft material, when the inlet flow passage and the outlet flow passage of the filter structural member are closed by the clamps simultaneously with completion of the returning operation, unlike the present invention, since the interior of the filter structural member is maintained at a positive pressure, a rapid flow from the filter structural member toward the collection line easily occurs when the clamps are opened to transition to the subsequent collection operation. Accordingly, the present invention is particularly useful in that, in the case that the filter accommodating unit is made of a soft material, it is possible to effectively prevent a rapid flow from the filter structural member toward the collection line.

The biological component collection device may be in the form of a plate-shaped cassette in which the collection line and the returning line are formed.

In accordance with such a configuration, simply by attaching the cassette to the separation device, the collection line and the returning line are arranged at predetermined positions of the separation device. Accordingly, it is possible to set up the biological component collection system simply and efficiently, thereby enhancing usability.

The cassette may comprise a first common line connected to a first end portion of the collection line and a first end portion of the returning line, and a second common line connected to a second end portion of the collection line and a second end portion of the returning line.

Consequently, since the number of ports provided in the cassette can be reduced, the structure of the cassette can be simplified.

The cassette may include a cassette body made of a soft material.

By such a configuration, compared to a conventional cassette made of a hard resin the entirety of which is manufactured by injection molding, the cassette can be manufactured at low cost.

Further, the present invention is characterized by a method of operating a biological component collection system, the biological component collection system comprising a separation device having a separation processing unit, and adapted to separate a biological component from a liquid containing at least one biological component; and a biological component collection device configured to be attachable to the separation device and having a flow path formed in the interior thereof, wherein the biological component collection device includes a collection line adapted to introduce the liquid containing at least one biological component from a donor, a returning line adapted to return an uncollected biological component to the donor, and a filter structural member provided in the returning line, the collection line and the returning line communicating with each other via a branching member, the separation device includes a collection and returning pump disposed in a line between the separation processing unit and the biological component collection device, and a clamp capable of opening and closing an inlet flow path and an outlet flow path of the filter structural member, and by driving the collection and returning pump, alternately carries out a collection operation of transferring the liquid containing at least one biological component from the donor to the separation processing unit via the collection line, and a returning operation for transferring an unnecessary biological component from the separation processing unit to the donor via the returning line, and wherein the method of operating the biological component collection includes a pressure release step of stopping a collection and returning pump at the end of the returning operation, and releasing a positive pressure inside the filter structural member, a clamp closure step of, after the pressure release step, closing an inlet flow passage and an outlet flow passage of the filter structural member by the clamp, and a collection operation starting step of, after the clamp closure step, starting a subsequent collection operation by driving the collection and returning pump.

The filter structural member may include a filter member, and a filter accommodating unit in which the filter member is accommodated, and the filter accommodating unit may be made of a soft material.

According to the biological component collection system and the method of operating the biological component collection system according to the present invention, it is possible to prevent blood having a high blood cell concentration from flowing out from the filter structural member when transitioning from the collection operation to a subsequent returning operation.

BRIEF DESCRIPTION OF DRAWINGS

FIG. 10 is a fifth explanatory diagram illustrating the operation of clamps;

FIG. 14A is an explanatory diagram of a pressure release step, FIG. 14B is an explanatory diagram of the clamp closure step, and FIG. 14C is an explanatory diagram of a collection operation starting step;

DESCRIPTION OF EMBODIMENTS

Preferred embodiments of a biological component collection system and a method of operating such a biological component collection system according to the present invention will be presented and described in detail below with reference to the accompanying drawings.

Figure 1:
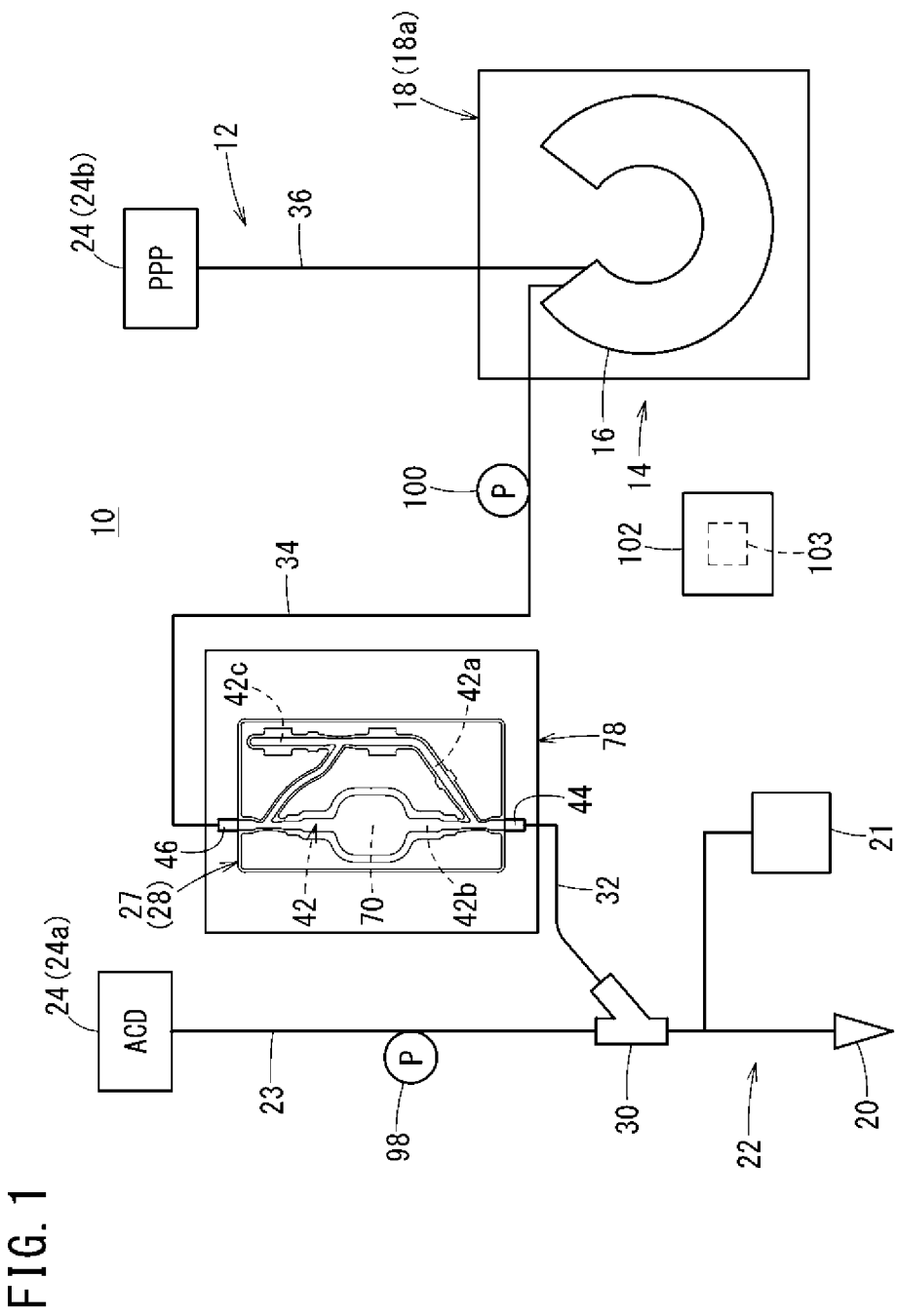
FIG. 1 is a schematic diagram of a blood component collection system according to an embodiment of the present invention.

As shown in FIG. 1, a blood component collection system 10, which is an embodiment of the biological component collection system, is constituted as a blood apheresis system, in which blood (whole blood) is continuously extracted from a blood donor and the blood is continuously extracted outside the body, whereby a specific blood component (in the present embodiment, plasma (platelet poor plasma: PPP)) is collected and the remaining blood components are returned to the blood donor. In the present embodiment, the blood is defined as "a liquid containing at least one biological component".

First, an outline description will be given of the blood component collection system 10 shown in FIG. 1. The blood component collection system 10 is equipped with a blood collection circuit set 12 for enabling storage and flow of blood components therein, a centrifugal separation device 14 (one form of a blood component separation device or a separation device) that applies a centrifugal force to the blood collection circuit set 12. The blood collection circuit set 12 includes a blood treatment unit 16 to which there is introduced whole blood that is removed from the blood donor, and the whole blood is centrifugally separated into a plurality of blood components. The centrifugal separation device 14 is equipped with a centrifuge unit 18 having a rotor 18a for applying a centrifugal force to the blood treatment unit 16. The blood treatment unit 16 is capable of being mounted in the centrifuge unit 18.

The blood collection circuit set 12 is discarded every time that it is used in order to prevent contamination and ensure sanitation. The blood collection circuit set 12 includes a blood collection and blood returning unit 22 having a blood collection needle 20 and an initial flow blood collection bag 21, a blood treatment unit 16, a plurality of bags 24, and a cassette 28 which is one form of a biological component collection device 27. The plurality of bags 24 include an ACD solution bag 24a containing an ACD solution which is an anticoagulant, and a PPP bag 24b for storing the plasma (platelet poor plasma).

The blood collection and blood returning unit 22 is connected to the ACD solution bag 24a and the cassette 28 via a tube connector 30. The ACD solution bag 24a is connected to the tube connector 30 via an ACD solution transfer tube 23.

The cassette 28 is connected to the blood collection and blood returning unit 22 via a donor side tube 32, and is also connected to the blood treatment unit 16 via a treatment unit side tube 34. The blood treatment unit 16 is attached to the centrifuge unit 18 (rotor 18a) of the centrifugal separation device 14, and is configured in the form of a container in which blood can be introduced therein, flow therethrough, and flow out therefrom. The PPP bag 24b is connected to the blood treatment unit 16 via a PPP transfer tube 36.

Figure 2:
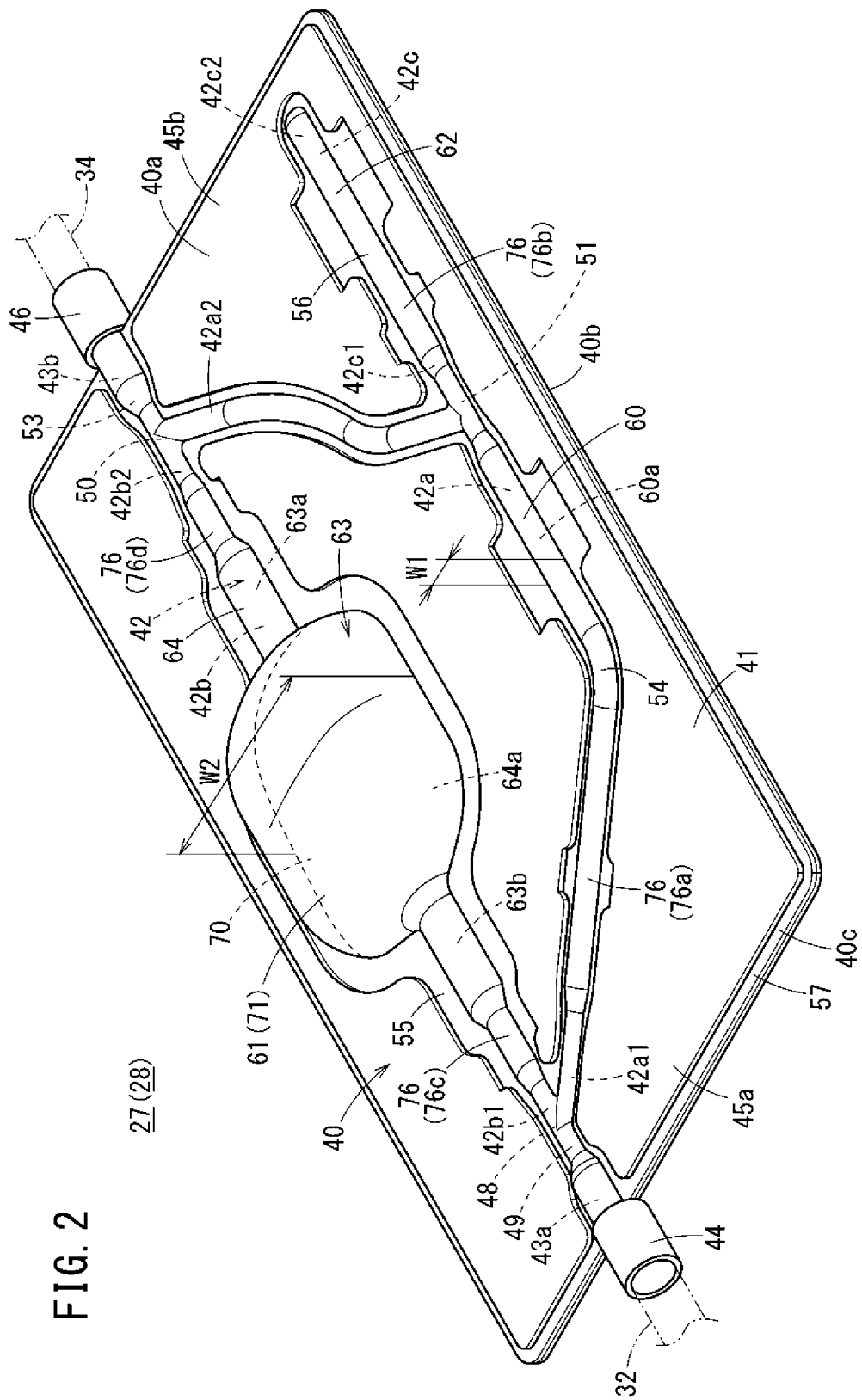
FIG. 2 is a perspective view of a cassette.

As shown in FIG. 2, the cassette 28 is provided with a cassette body 40 in which a flow path 42 is formed. The cassette body 40 is formed in a rectangular shape as viewed in plan. The cassette body 40 is formed of a soft material. For the soft material that constitutes the cassette body 40, the same material is used over the entirety of the cassette body 40. Moreover, the cassette body 40 may be constituted from a plurality of different materials. More specifically, the cassette body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

A flow path 42 is formed between the first sheet 40a and the second sheet 40b. Fusion bonding (high frequency fusion bonding, thermal fusion bonding, etc.) is used as the means for joining the first sheet 40a and the second sheet 40b. The first sheet 40a and the second sheet 40b may also be joined together by another joining means (adhesion or the like). Further, a first port member 44 and a second port member 46, which are made of a hard material (for example, polypropylene, polycarbonate, or the like), are disposed on an outer peripheral edge portion 40c of the cassette body 40.

The first port member 44 is provided at a first end portion 45a, which is one longitudinal end portion of the rectangular cassette body 40, and is connected to a first port 43a provided on one end side of the flow path 42. The second port member 46 is provided at a second end portion 45b, which is another longitudinal end portion of the cassette body 40, and is connected to a second port 43b provided on the other end side of the flow path 42. The donor side tube 32 and the treatment unit side tube 34 are connected respectively to the port members 44, 46.

The flow path 42 that is formed in the cassette body 40 includes a collection line 42a through which blood flows when the centrifugal separation device 14 is in operation, a returning line 42b in which the filter member 70 is arranged, a filter structural member 63 disposed in the returning line 42b, and a hollow portion 42c through which blood and blood components do not flow during operation of the centrifugal separation device 14. A first end portion 42a1 of the collection line 42a and a first end portion 42b1 of the returning line 42b are connected to a first common line 49 via a first coupling member 48. A second end portion 42a2 of the collection line 42a and a second end portion 42b2 of the returning line 42b are connected to a second common line 53 via a second coupling member 50. Accordingly, in the flow path 42, the collection line 42a and the returning line 42b are connected in parallel. The first common line 49 communicates with the first port 43a. The second common line 53 communicates with the second port 43b.

A first end portion 42c1 of the hollow portion 42c is connected to an intermediate part of the collection line 42a via the third coupling member 51. A second end portion 42c2 of the hollow portion 42c is closed. The collection line 42a and the returning line 42b extend at least partially in parallel with each other. The hollow portion 42c is formed in a straight line shape, and is connected in series to a portion of the collection line 42a that extends in parallel with the returning line 42b. At least a part of the collection line 42a extends between the hollow portion 42c and the returning line 42b, which extend in parallel. The first coupling member 48, the second coupling member 50, and the third coupling member 51 each constitute a portion of the flow path 42.

In the cassette body 40, seal, members 55 in the form of fusion-bonded locations are formed along the flow path 42 on both sides of the flow path 42. Further, a seal member 57 is formed along the outer peripheral edge portion 40c, on the outer peripheral edge portion 40c of the cassette body 40.

In the cassette body 40, even if there is no positive pressure acting within the flow path 42, the wall portions that form the flow path 42 bulge in convex shapes in the thickness direction of the cassette 28 on both side surfaces of the cassette body 40. Accordingly, the flow path 42 is a flow path which is opened in its natural state. When pressed by an external force, the wall portions can be elastically deformed in directions to close the flow path 42 at the pressed location thereof.

The cassette body 40 comprises a collection line forming member 54 forming the collection line 42a, a returning line forming member 64 forming the returning line 42b, and a hollow portion forming member 56 forming the hollow portion 42c.

The collection line forming member 54 includes a first pressed soft portion 60 made of a soft material. The first pressed soft portion 60 forms a first flow path region 60a which is one part of the flow path 42. In order to measure the internal pressure of the flow path 42 during operation of the centrifugal separation device 34, in a state (hereinafter referred to as a "cassette attached state") in which the cassette 28 is attached to the centrifugal separation device 14, the first pressed soft portion 60 is a site that is pressed by a later-described first load detecting unit 88 which is installed in the centrifugal separation device 14.

The returning line forming member 64 includes a second pressed soft portion 61 made of a soft material. The second pressed soft portion 61 forms a second flow path region 64a which is another part of the flow path 42. In the cassette attached state, in order to acquire data for the purpose of correcting a calibration curve L (see FIG. 13), which is reference data to be used when calculating the circuit internal pressure using the load detected by the first load detecting unit 88, the second pressed soft portion 61 is a site that is pressed by a later-described second load detecting unit 89 which is installed in the centrifugal separation device 14.

The filter structural member 63 includes the filter member 70, and a filter accommodating unit 71 in which the filter member 70 is accommodated. The filter accommodating unit 71 makes up a portion of the cassette body 40. Accordingly, the filter accommodating unit 71 is also made of a soft material. An inlet flow passage 63a for introducing blood components into the filter structural member 63 is formed between the filter accommodating unit 71 and the second end portion 42b2 of the returning line 42b. An outlet flow passage 63b for enabling the blood components to flow out from the filter structural member 63 is formed between the filter accommodating unit 71 and the first end portion 42b1 of the returning line 42b.

Figure 3:
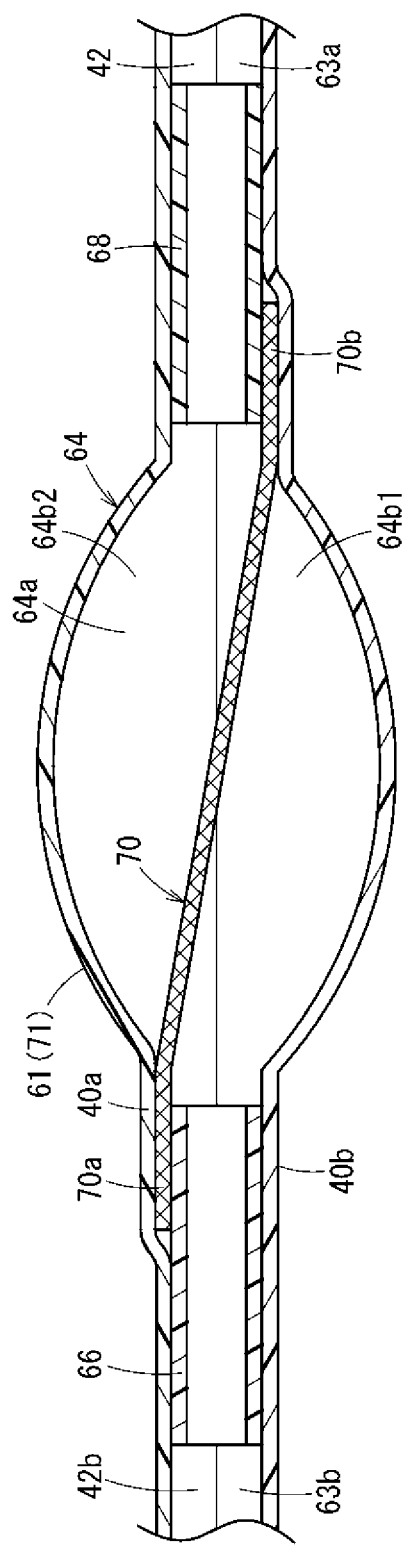
FIG. 3 is a cross-sectional view of the cassette.

In the present embodiment, the second pressed soft portion 61 constitutes a filter accommodating unit 71. As shown in FIG. 3, a filter member 70 in the form of a sheet mesh is disposed inside the filter accommodating unit 71 for the purpose of removing clotted blood or blood clumps contained within the blood or the blood components. A first tube member 66 and a second tube member 68 are disposed in the returning line 42b at positions on both sides of the filter accommodating unit 71. By the filter member 70, the internal space of the filter accommodating unit 71 is partitioned into a first space 64b1 that communicates with the first tube member 66, and a second space 64b2 that communicates with the second tube member 68.

The first tube member 66 is joined by fusion bonding or the like to the first sheet 40a and the second sheet 40b. A first end portion 70a of the filter member 70 is disposed between the first tube member 66 and the first sheet 40a. The first sheet 40a, the first end portion 70a of the filter member 70, and the first tube member 66 are joined to each other mutually by fusion bonding or the like. The second tube member 68 is joined by fusion bonding or the like to the first sheet 40a and the second sheet 40b. A second end portion 70b of the filter member 70 is disposed between the second tube member 68 and the second sheet 40b. The second sheet 40b, the second end portion 70b of the filter member 70, and the second tube member 68 are joined to each other mutually by fusion bonding or the like.

In FIG. 2, the second pressed soft portion 61 is more easily deformable than the first pressed soft portion 60. In the present embodiment, the width W2 of the second pressed soft portion 61 is greater than the width W1 of the first pressed soft portion 60, whereby the second pressed soft portion 61 is more easily deformable than the first pressed soft portion 60. The ratio of the width W2 of the second pressed soft portion 61 with respect to the width W1 of the first pressed soft portion 60 is set, for example, to 300% or greater, preferably is set to 500% or greater, and more preferably, is set to 800% or greater.

Moreover, the width of the wall portion that constitutes the second pressed soft portion 61 may be set to be thinner than the width of the wall portion of the first pressed soft portion 60, whereby the second pressed soft portion 61 may be more easily deformable than the first pressed soft portion 60. Alternatively, the second pressed soft portion 61 may be made of a material that is softer than that of the first pressed soft portion 60, whereby the second pressed soft portion 61 may be more easily deformable than the first pressed soft portion 60.

The hollow portion forming member 56 includes a third pressed soft portion 62 made of a soft material. In the cassette attached state, the third pressed soft portion 62 is a site that is pressed by a later-described third load detecting unit 90 which is installed in the centrifugal separation device 14. The hollow portion 42c communicates with the collection line 42a via the third coupling member 51.

The first pressed soft portion 60, the second pressed soft portion 61, and the third pressed soft portion 62 constitute respective parts of the flow path 42. Accordingly, the first pressed soft portion 60, the second pressed soft portion 61, and the third pressed soft portion 62 bulge out in the thickness direction of the cassette body 40, from a sheet surface 41 (base surface) of the cassette body 40. The first pressed soft portion 60 and the third pressed soft portion 62 are formed to have the same shape and the same size as each other. Accordingly, the first pressed soft portion 60 and the third pressed soft portion 62 are formed mutually with the same rigidity.

On the cassette 28, there are provided a plurality of clamp action members 76 (76a to 76d) on which a plurality of clamps 72 (72a to 72d) (see FIG. 4), which act as flow path opening/closing mechanisms, are provided in the centrifugal separation device 14. When the cassette 28 is installed in the centrifugal separation device 14, the clamp action members 76 abut against or are placed in facing relation to their corresponding clamps 72. More specifically, the clamp action member 76a is disposed at a location forming an end portion of the collection line 42a in the cassette 28 on the side of the first port member 44. The clamp action member 76b is disposed between the third pressed soft portion 62 and the third coupling member 51 (at a location of the hollow portion 42c in the vicinity of the third coupling member 51). The clamp action members 76c, 76d are disposed respectively at locations forming both end portions of the returning line 42b.

Moreover, the flow path structure formed in the cassette 28, and the number and arrangement of the bags 24 that are provided are not limited to the configurations shown and described above, but may be modified in accordance with the type of blood components to be collected, the method of use, and the like.

In a method for manufacturing the cassette 28 having the above-described configuration, there are included a molding step in which the first sheet 40a and the second sheet 40b are superimposed on each other, and the first sheet 40a and the second sheet 40b are fusion bonded together so as to form the flow path 42 between the first sheet 40a and the second sheet 40b, to thereby mold the cassette 28 equipped with the cassette body 40, and a sterilization step of sterilizing the cassette 28 obtained by the aforementioned molding step.

In the molding step, for example, a sheet-shaped material is fed out from two material rolls on which there are wound, respectively, sheet materials that serve as the materials for the first sheet 40a and the second sheet 40b, and the assembly components (the filter member 70, the port members 44, 46) are supplied together therewith to a joining device such as a high-frequency fusion bonding device or the like. The joining device is equipped with upper and lower molds, and by carrying out blow molding while the two sheet-shaped materials are joined together with the assembly components, the cassette 28 is molded with the flow path 42 formed therein. In this case, the tubes 32, 34 may be connected at the time that the cassette 28 is molded in the joining device.

In the sterilization step, the entirety of the blood collection circuit set 12 including the plurality of bags 24 (ACD solution bag 24a, etc.) may be sterilized. Consequently, the blood collection circuit set 12 can be sterilized efficiently.

In FIG. 1, the centrifugal separation device 14 is a device that is used repeatedly during blood component collection, and is provided, for example, in a medical facility, a blood collection vehicle, or the like. The centrifugal separation device 14 is equipped with the centrifuge unit 18 having the rotor 18a, and a cassette mounting unit 78 to which the cassette 28 of the blood collection circuit set 12 is capable of being attached.

Figure 4:
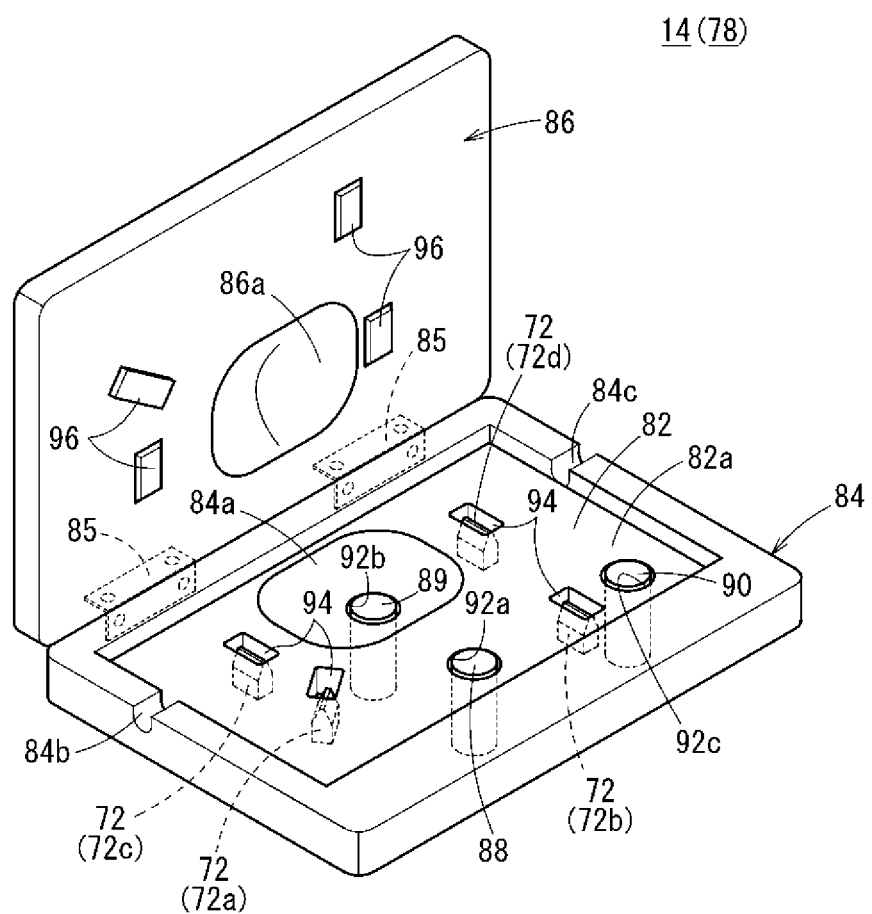
FIG. 4 is a perspective view of a cassette mounting unit.

As shown in FIG. 4, the cassette mounting unit 78 includes an attachment base 84 having a cassette mounting groove 82 formed therein, a lid 86 which can be opened and closed and is configured in a manner to cover the attachment base 84 when closed, and a plurality of clamps 72 configured to be capable of pressing the clamp action members 76 of the cassette 28. The cassette mounting unit 78 is further equipped with a first load detecting unit 88 which is capable of pressing the first pressed soft portion 60 (see FIG. 2) of the cassette 28, a second load detecting unit 89 which is capable of pressing the second pressed soft portion 61 (see FIG. 2) of the cassette 28, and a third load detecting unit 90 which is capable of pressing the third pressed soft portion 62 (see FIG. 2) of the cassette 28.

A first port arrangement groove 84b into which the first port member 44 of the cassette 28 can be arranged, and a second port arrangement groove 84c into which the second port member 46 of the cassette 28 can be arranged are provided on the outer peripheral portion of the attachment base 84. The first port arrangement groove 84b and the second port arrangement groove 84c are in communication with the cassette mounting groove 82.

The lid 86 is connected in a rotatable manner to the attachment base 84 via a hinge 85. When the lid 86 is closed with the cassette 28 being held in the cassette mounting groove 82 of the attachment base 84, the cassette 28 is sandwiched between the attachment base 84 and the lid 86. On the attachment base 84 and the lid 86, there are respectively provided concave portions 84a, 86a in which the filter accommodating unit 71 of the cassette 28 can be received. Consequently, the cassette 28 is appropriately retained between the attachment base 84 and the lid 86, while also preventing the filter accommodating unit 71 from being crushed. Further, the concave portions 84a, 86a prevent the filter accommodating unit 71 from bulging excessively.

The first load detecting unit 88 is inserted into a first through hole 92a provided in the attachment base 84, together with being exposed in the cassette mounting groove 82. The second load detecting unit 89 is inserted into a second through hole 92b provided in the attachment base 84, together with being exposed in the concave portion 84a provided in the cassette mounting groove 82. The third load detecting unit 90 is inserted into a third through hole 92c provided in the attachment base 84, together with being exposed in the cassette mounting groove 82. An upper surface of the first load detecting unit 88 and an upper surface of the third load detecting unit 90 protrude respectively from a bottom surface 82a of the cassette mounting groove 82. An upper surface of the second load detecting unit 89 protrudes from a bottom surface of the concave portion 84a.

The protruding height of the first load detecting unit 88 from the bottom surface 82a is the same as the protruding height of the third load detecting unit 90 from the bottom surface 82a. The first load detecting unit 88, the second load detecting unit 89, and the third load detecting unit 90 are constituted from load cells, for example.

The plurality of clamps 72 (72a to 72d) are capable of being advanced and retracted in the cassette thickness direction in a state in which the cassette 28 is retained in the cassette mounting groove 82, and are disposed corresponding to the arrangement of the plurality of clamp action members 76 (76a to 76d) provided on the cassette 28. The plurality of clamps 72 are capable of pressing the plurality of clamp action members 76, respectively, via a plurality of holes 94 that open on a bottom surface 82a of the cassette mounting groove 82. When closed, a plurality of projections 96 are provided on the lid 86 at positions corresponding to the plurality of holes 94 (clamps 72).

At a time that the clamp action members 76 are not being pressed by the clamps 72, in a state in which the cassette 28 is mounted in the cassette mounting unit 78, the flow paths inside the clamp action members 76 are opened. When the clamps 72 protrude from the holes 94 and press the clamp action members 76, the flow paths inside the clamp action members 76 are closed. In addition, when the clamps 72 are retracted, due to the elastic restorative force of (the clamp action members 76 of) the cassette body 40, the clamp action members 76 are restored to their original shape, and the flow paths inside the clamp action members 76 are opened.

As shown in FIG. 1, the centrifugal separation device 14 includes an ACD solution transfer pump 98 which acts on the ACD solution transfer tube 23, and a collection and returning pump 100 which acts on the treatment unit side tube 34 that is connected to the cassette 28. The ACD solution transfer pump 98 is a pump that transfers the ACD solution from the ACD solution bag 24a to the cassette 28 and the blood treatment unit 16 via the ACD solution transfer tube 23. The collection and returning pump 100 is a pump that transfers blood from the blood donor to the blood treatment unit 16, and together therewith, transfers blood from the blood treatment unit 16 back to the blood donor. The ACD solution transfer pump 98 and the collection and returning pump 100 are constituted, for example, by a roller pump or a finger pump.

The centrifugal separation device 14 further includes a control unit 102 adapted to control the centrifuge unit 18, the cassette mounting unit 78, and the pumps 98, 100. The operations of the aforementioned plurality of clamps 72 are controlled by the control unit 102. The control unit 102 includes a computation unit 103 which, when the centrifugal separation device 14 is in operation, acquires (calculates) the circuit internal pressure of the blood collection circuit set 12, on the basis of the loads detected by the first load detecting unit 88 and the third load detecting unit 90 (see FIG. 4).

The centrifugal separation device 14, using the data acquired by the second load detecting unit 89, corrects the slope of the calibration curve L (see FIG. 13) that is used when calculating the circuit internal pressure, and calculates the circuit internal pressure of the cassette 28 using the data acquired by the first load detecting unit 88, and the corrected calibration curve La. Details concerning the inclination correction of the calibration curve L will be described later.

Next, operations of the blood component collection system 10 according to the present embodiment, which is configured in the manner described above, will be described.

As a preparation (set-up) for collecting blood components from a blood donor using the blood component collection system 10 shown in FIG. 1, the blood collection circuit set 12 is attached to the centrifugal separation device 14. More specifically, the cassette 28 is mounted in the cassette mounting unit 78, and the blood treatment unit 16 is attached to the rotor 18a. On the other hand, the blood collecting needle 20 pierces and is inserted into the blood donor.

Figure 5:
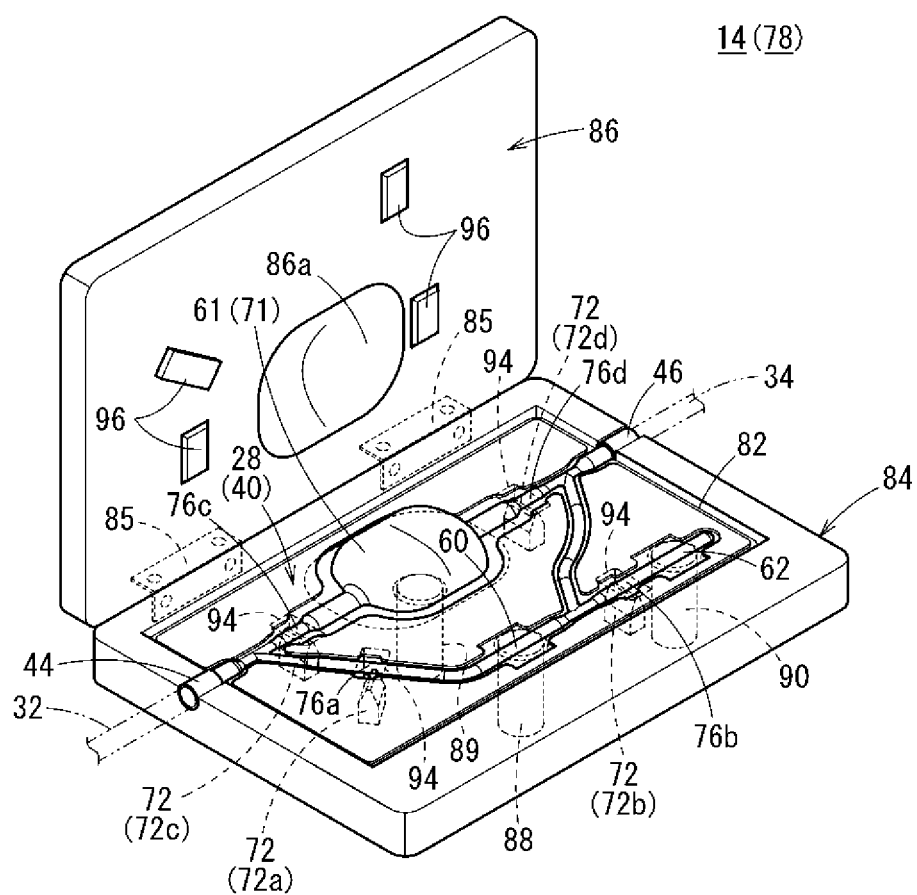
FIG. 5 is a perspective view of the cassette mounting unit with a cassette mounted therein.

When the cassette 28 is mounted in the cassette mounting unit 78, as shown in FIG. 5, at first, the cassette 28 is mounted in the cassette mounting groove 82. In addition, by closing the lid 86, the cassette 28 is placed in a state of being held between the lid 86 and the attachment base 84. As a result, the first pressed soft portion 60, the second pressed soft portion 61, and the third pressed soft portion 62 of the cassette 28 are pressed respectively by the first load detecting unit 88, the second load detecting unit 89, and the third load detecting unit 90, and are placed in a state of being slightly elastically deformed. In this case, the amount of deformation of the first pressed soft portion 60 due to being pressed by the first load detecting unit 88 is the same as the amount of deformation of the third pressed soft portion 62 due to being pressed by the third load detecting unit 90. Further, the plurality of clamp action members 76 of the cassette 28 are placed in facing relation with respect to the plurality of clamps 72.

When a command is issued by operation of a user with respect to the centrifugal separation device 14 shown in FIG. 1 in order to initiate operations, in the centrifugal separation device 14, after having carried out a later-described calibration process (a correction to the slope of the calibration curve), then under the action of the ACD solution transfer pump 98, priming with the ACD solution is carried out. More specifically, at a stage at which it is detected by a non-illustrated line sensor disposed outside of the cassette 28 that the ACD solution has arrived in the immediate vicinity of the flow path 42, priming by the ACD solution is terminated.

Next, by rotating the rotor 18a, the centrifugal separation device 14 applies a centrifugal force to the blood treatment unit 16 that is attached to the rotor 18a, and together therewith, by operation of the collection and returning pump 100, blood (whole blood) from the blood donor is extracted and introduced into the blood treatment unit 16 (blood collection operation). By the centrifugal force that accompanies rotation of the rotor 18a, the blood introduced into the blood treatment unit 16 is separated into red blood cells (concentrated red blood cells), a buffy coat, and plasma (platelet poor plasma).

The plasma that is separated in the blood treatment unit 16 is introduced into the PPP bag 24b via the PPP transfer tube 36. After completion of the centrifugal separation process, the remaining blood components (the red blood cells and the buffy coat) are returned to the blood donor (returning operation). At this time, since foreign substances such as blood clumps and the like contained within the remaining blood components are trapped by the filter member 70 provided in the returning line 42b of the cassette 28, any risk of such foreign matter being returned to the blood donor can be reduced. The collection operation and the returning operation described above are repeated alternately a plurality of times.

During operation of the blood component collection system 10, the clamps 72 (see FIG. 4) of the centrifugal separation device 14 are operated in the following manner.

Figure 6:
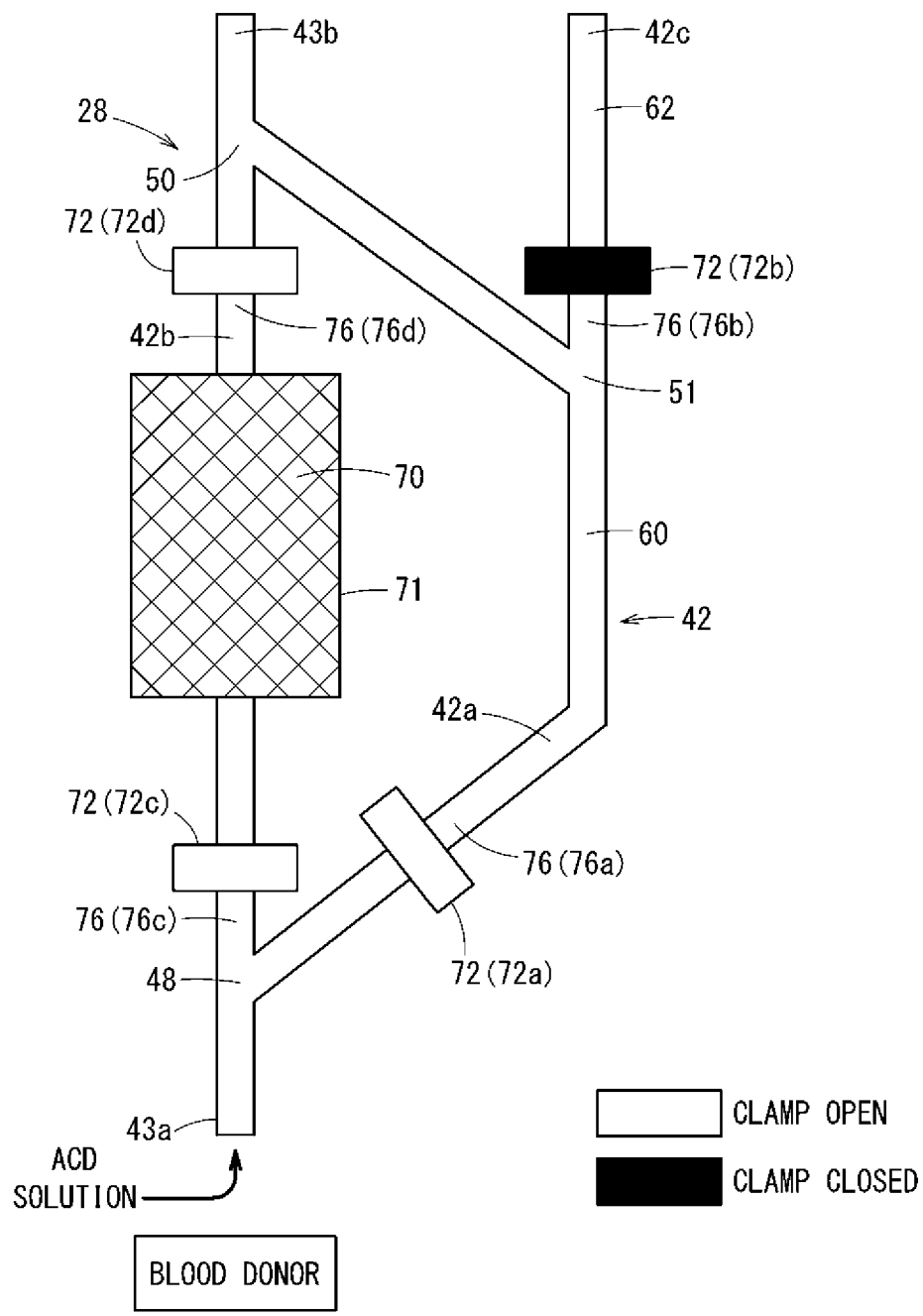
FIG. 6 is a first explanatory diagram illustrating the operation of clamps.

As shown in FIG. 6, when priming is carried out by the ACD solution, the clamp 72b is closed, and the clamps 72a, 72c, and 72d are opened. Consequently, a state is brought about in which the hollow portion 42c is cut off from other parts of the flow path 42. In addition, in this state, priming by the ACD solution is terminated at a stage at which it is detected by a non-illustrated line sensor outside the cassette 28 in the immediate vicinity of the first port 43a that the ACD solution has arrived in close proximity to the first port 43a.

Figure 7:
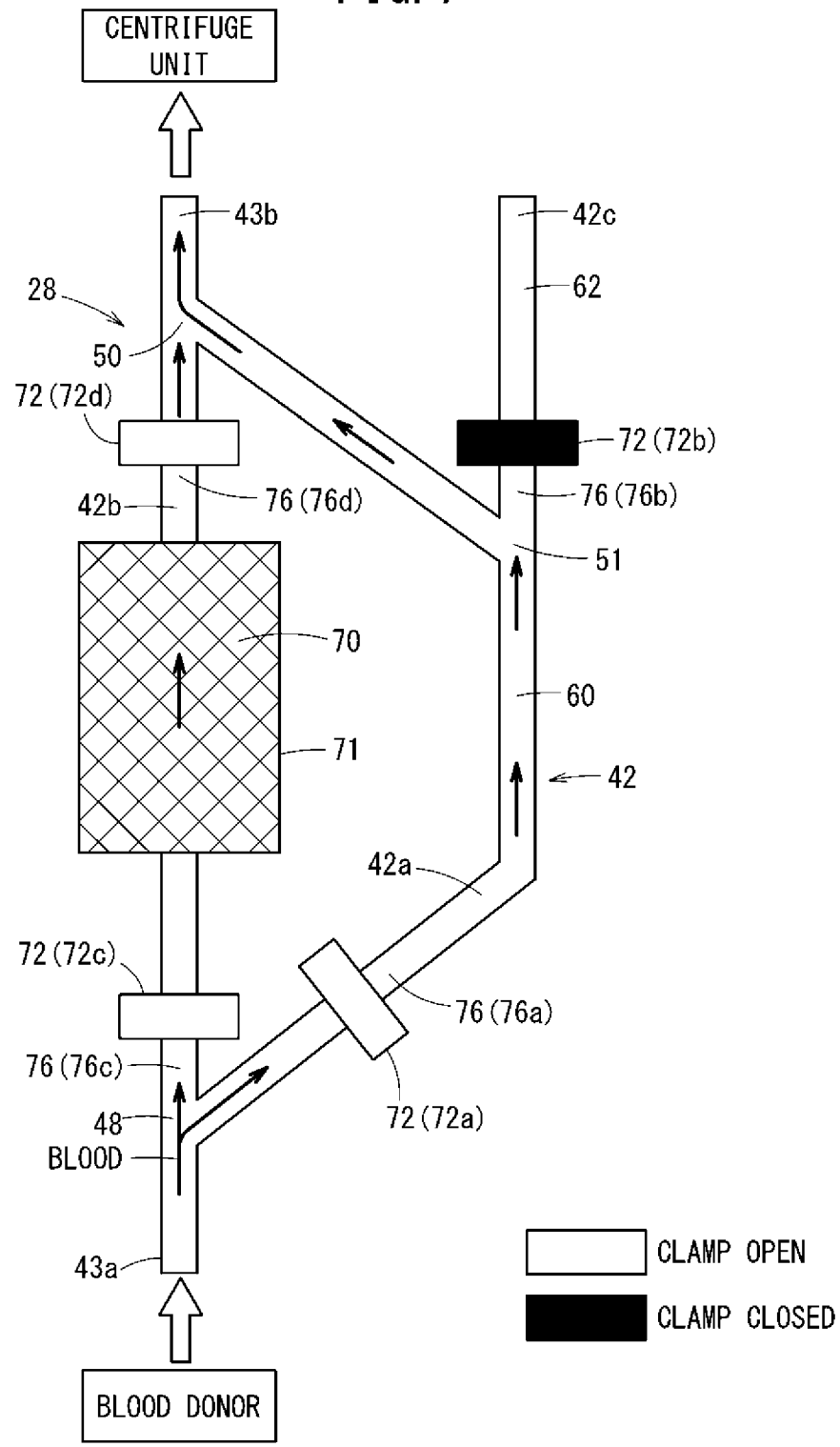
FIG. 7 is a second explanatory diagram illustrating the operation of clamps.

Next, when blood collection is performed for the first time, as shown in FIG. 7, the state in which the clamp 72b is closed and the clamps 72a, 72c, and 72d are opened is maintained. In addition, in this state, blood from the blood donor is introduced into the flow path 42 other than the hollow portion 42c of the cassette 28, and all of the air inside the circuit of the cassette 28 is pushed out by the blood into the blood treatment unit 16.

Figure 8:
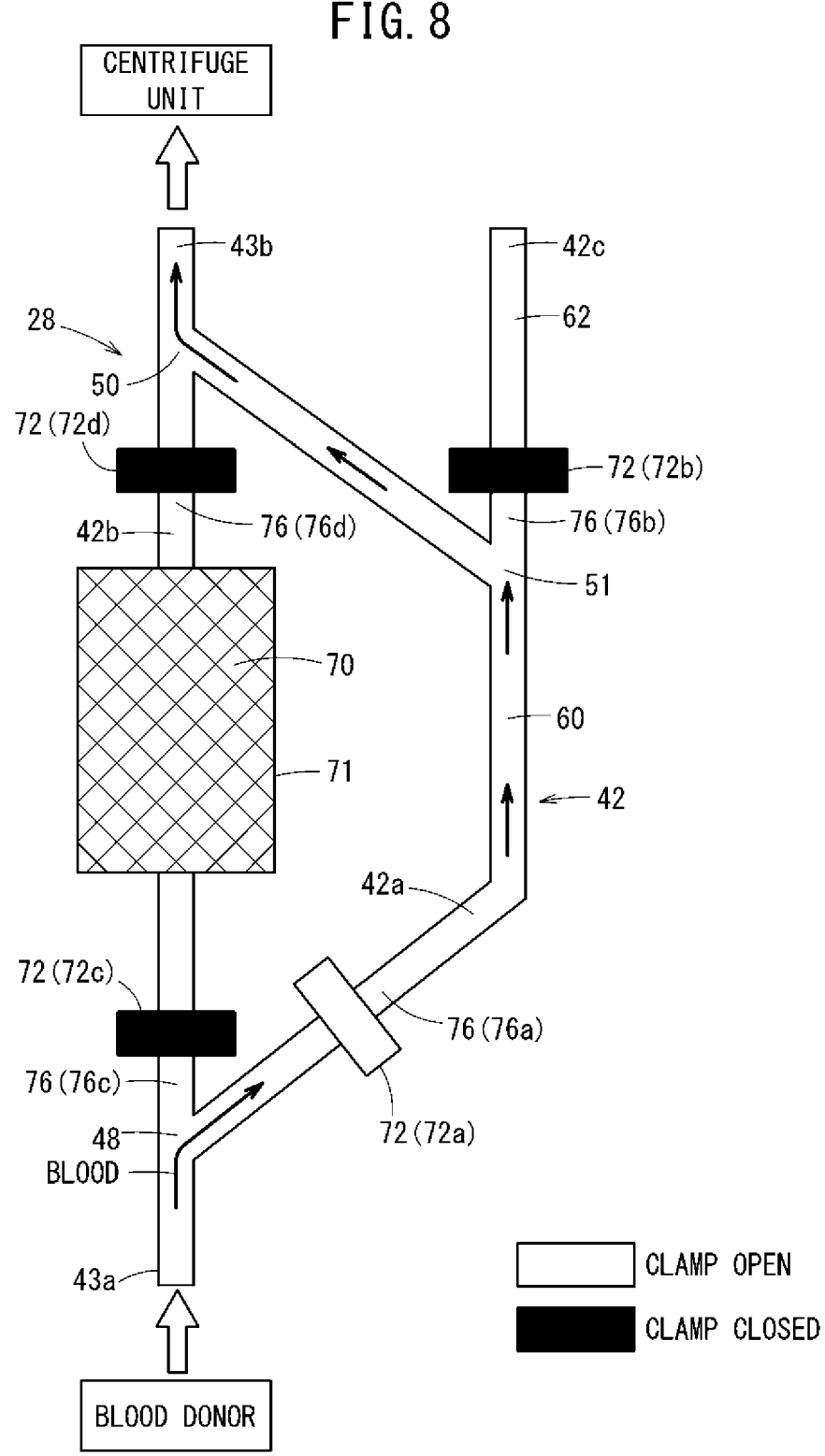
FIG. 8 is a third explanatory diagram illustrating the operation of clamps.

During the course of the initial blood collection, as shown in FIG. 8, by closing the clamps 72c and 72d, the returning line 42b is closed. Consequently, a negative pressure is prevented from acting on the filter accommodating unit 71 and blocking the filter accommodating unit 71. Hereinafter, the open and closed state of the plurality of clamps 72 shown in FIG. 8 will be referred to as a "collection mode clamping state".

Figure 9:
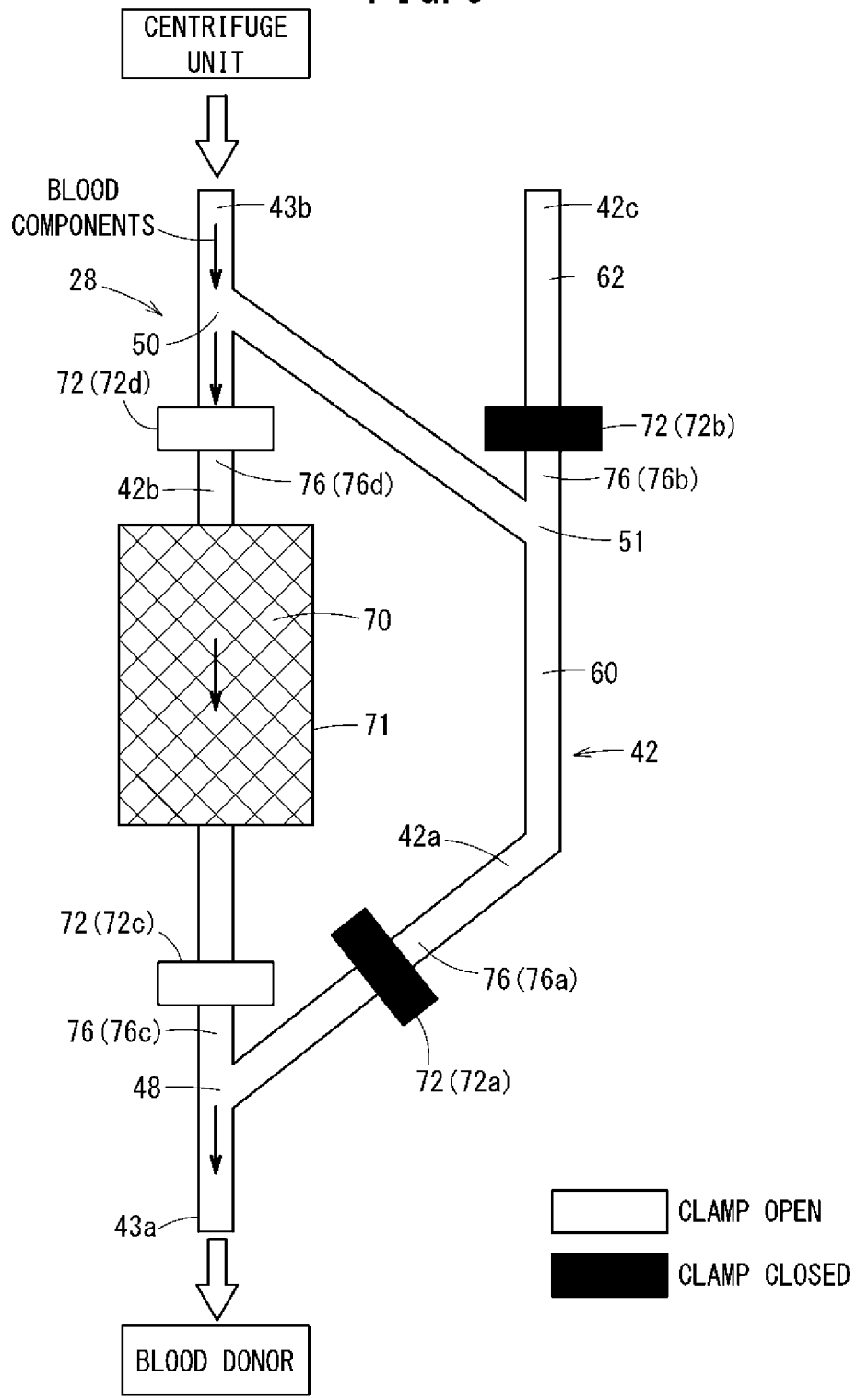
FIG. 9 is a fourth explanatory diagram illustrating the operation of clamps.

Next, when return of the blood components to the blood donor is carried out, as shown in FIG. 9, the clamp 72a is closed, and the clamps 72c and 72d are opened. Thus, the collection line 42a is closed, whereas the returning line 42b is opened. Accordingly, when the blood components pass through the filter member 70, clotted blood contained within the blood components is trapped in the filter member 70. Since the collection line 42a is closed, clotted blood cannot be returned to the donor via the collection line 42a. Hereinafter, the open and closed state of the plurality of clamps 72 shown in FIG. 9 will be referred to as a "returning mode clamping state".

Next, when second and subsequent blood collections are carried out, as shown in FIG. 10, the clamps 72c and 72d are closed, and the clamp 72a is opened. Thus, the returning line 42b is closed, whereas the collection line 42a is opened. Accordingly, from among the collection line 42a and the returning line 42b, blood is transferred via only the collection line 42a to (the centrifuge unit 18 of) the blood treatment unit 16. Thereafter, return of the blood (see FIG. 9) is carried out again. Collection of blood and return of the blood in this manner are repeated a plurality of times.

In addition, when return of the blood is performed for the last time, the clamp 72a is closed, the clamps 72c and 72d are opened, and the plurality of clamps 72 are again set to the returning mode clamping state shown in FIG. 9.

Next, a circuit internal pressure acquisition method in which the blood component collection system 10 is used will be described.

In the circuit internal pressure acquisition method, there are included a calibration step S1 of correcting a calibration curve L (see FIG. 13) used when calculating the circuit internal pressure prior to introducing blood from the blood donor into the flow path 42 of the cassette 28, and a pressure measurement step S2 of measuring the circuit internal pressure of the cassette 28 at a time of normal operation (during blood treatment) of the centrifugal separation device 14.

Figure 11A:
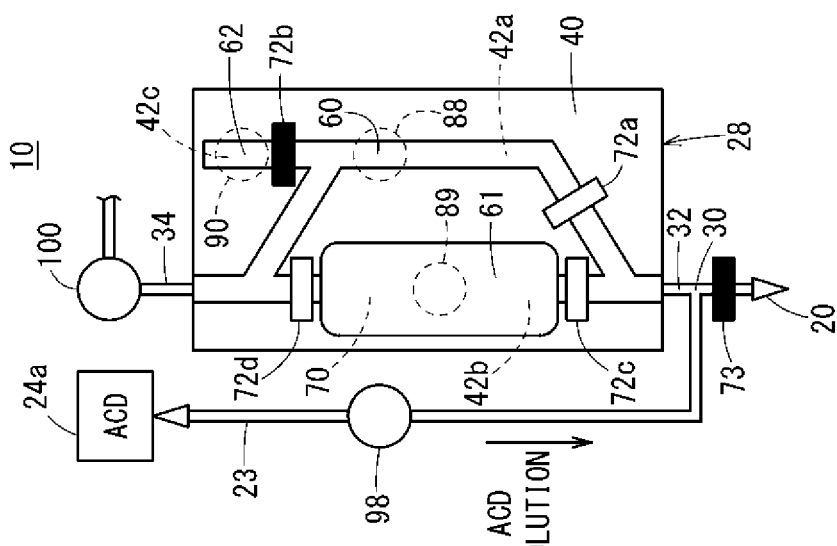
FIG. 11A is a first explanatory diagram of a circuit internal pressure acquisition method.

More specifically, the calibration step includes a pressure raising step, a data acquisition step, and a slope correction step. In the pressure raising step, before blood from the donor is introduced into the flow path 42 of the cassette 28, a fluid other than blood is introduced into the flow path 42 to thereby raise the circuit internal pressure. In this case, first, as shown in FIG. 11A, in a state in which the ACD solution transfer tube 23 is disconnected from the ACD solution bag 24a (see FIG. 1), the clamp 72b is closed, and the hollow portion 42c is placed in a non-communicative state with respect to the collection line 42a and the returning line 42b. Consequently, the hollow portion 42c is spatially separated from the collection line 42a and the returning line 42b. At this time, the clamps 72a, 72c, and 72d are opened.

Figure 11B:
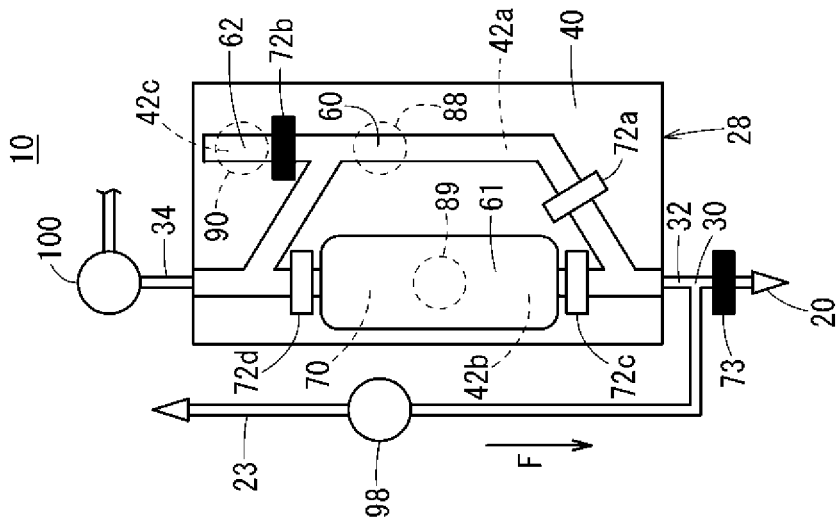
FIG. 11B is a second explanatory diagram of the circuit internal pressure acquisition method.

Next, as shown in FIG. 11B, the tube 32 which is more on the side of the blood collecting needle 20 (blood donor side) than the tube connector 30 is closed by the clamp 73, together with driving the ACC solution transfer pump 98, so that, for example, air as a fluid F is delivered into the circuit (the collection line 42a and the returning line 42b) of the cassette 28. At this time, by stopping the collection and returning pump 100, the collection line 42a and the returning line 42b are raised in pressure accompanying the introduction of air therein by driving the ACD solution transfer pump 98. Consequently, the first load detecting unit 88 detects the load received from the first pressed soft portion 60, and the second load detecting unit 89 detects the load received from the second pressed soft portion 61.

Next, in the data acquisition step, the load received from the second pressed soft portion 61, in a state in which the pressurized fluid (in this case, air) is introduced into the second flow path region 64a, is detected by the second load detecting unit 89, whereby data is acquired for correcting the calibration curve L (see FIG. 13) which is used when calculating the circuit internal pressure.

Figure 12:
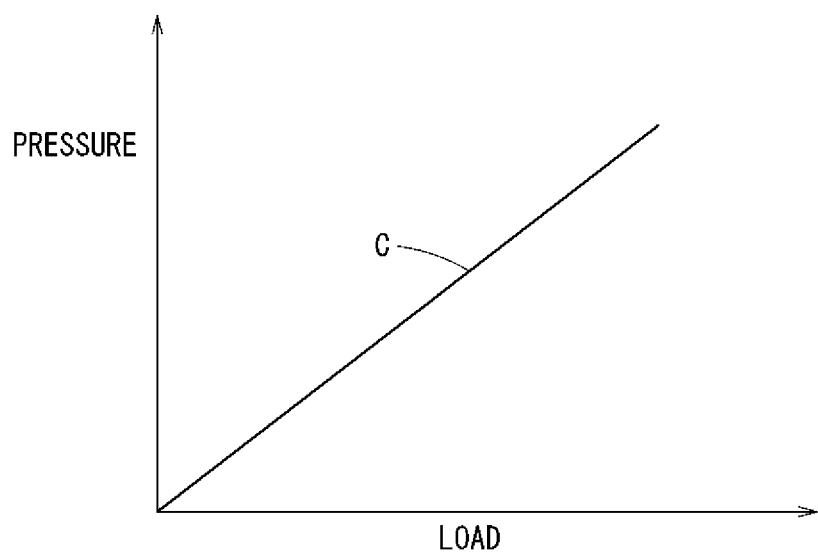
FIG. 12 is a diagram showing a load-pressure curve illustrating a relationship between a load detected by a second load detecting unit and the circuit internal pressure.

In this instance, as shown in FIG. 12, a relationship between the load detected by the second load detecting unit 89 and the circuit internal pressure is indicated by a load-pressure curve C. The load-pressure curve C is substantially the same, irrespective of the material and the manufacturing method of the cassette body 40. The load-pressure curve C can be acquired in advance by experiment or analysis. The centrifugal separation device 14 retains (stores) the load-pressure curve C in the control unit 102. The centrifugal separation device 14 may also access an external database in which the load-pressure curve C is stored, and may refer to the load-pressure curve C.

Figure 13:
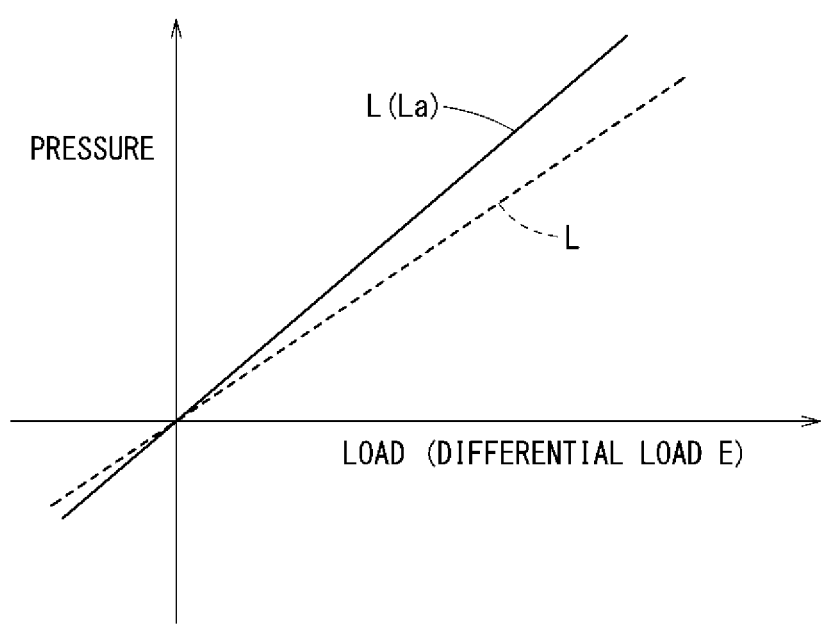
FIG. 13 is a diagram showing a calibration curve used for calculating the circuit internal pressure.

Thus, the centrifugal separation device 14 acquires the circuit internal pressure (data) at a point in time of having been raised in pressure by the air, with reference to the load-pressure curve C, and on the basis of the load detected by the second load detecting unit 89. Additionally, in the slope correction step, the slope of the calibration curve L is corrected as shown in FIG. 13, using the data acquired by the second load detecting unit 89. More specifically, concerning the relationship (calibration curve) between the load and the pressure, a correlation between air and blood is previously set in advance, and on the basis of such a correlation, the slope of the blood calibration curve L is corrected using the air data acquired by the second load detecting unit 89. Consequently, the calibration curve La, the slope of which has been corrected, is obtained.

Figure 11C:
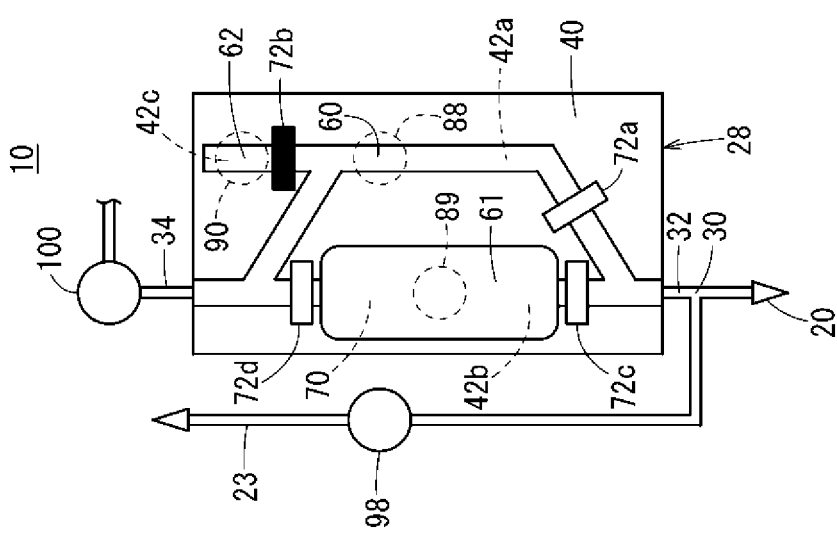
FIG. 11C is a third explanatory diagram of the circuit internal pressure acquisition method

Next, as shown in FIG. 11C, the ACD solution transfer tube 23 is connected to the ACD solution bag 24a, and together therewith, an operation (the aforementioned priming) is carried out to drive the ACD solution transfer pump 98, until the ACD solution is filled until just before the flow path 42 of the cassette 28.

Next, the blood component collection system 10 carries out the pressure measurement step. The pressure measurement step includes a blood introduction step, a first measurement step, a second measurement step, a differential load calculation step, and an internal pressure calculation step.

In the blood introduction step, blood is introduced into the flow path 42 of the cassette 28 (see FIGS. 7 to 10). In the first measurement step, in a state in which blood is being delivered to the collection line 42a, the collection line forming member 54 is pressed, and the load $\alpha 1$ that accompanies pressing of the collection line forming member 54 is measured. More specifically, the load received from the first pressed soft portion 60 is detected by the first load detecting unit 88. In the second measurement step, in a state in which blood is not being delivered to the hollow portion 42c, the hollow portion forming member 56 is pressed, and the load $\alpha 2$ that accompanies pressing of the hollow portion forming member 56 is measured. More specifically, the load received from the third pressed soft portion 62 is detected by the third load detecting unit 90.

In the differential load calculation step, the differential load $\alpha$, which is obtained by subtracting the load $\alpha 2$ measured in the second measurement step from the load $\alpha 1$ measured in the first measurement step, is calculated. In the internal pressure calculation step, the internal pressure (circuit internal pressure) of the collection line 42a is calculated on the basis of the calculated differential load $\alpha$. In this case, the centrifugal separation device 14 calculates the circuit internal pressure using the corrected calibration curve La (see FIG. 13).

In actuality, the reaction force, which is based on the elastic restorative force of the first pressed soft portion 60, and the reaction force, which is based on the elastic restorative force of the third pressed soft portion 62, do not match one another completely. Therefore, before calculating the differential load $\alpha$, a step of making $\alpha 1$ and $\alpha 2$ match one another is performed under the same condition (a state in which blood is not delivered to either the collection line 42a or the hollow portion 42c). More specifically, a correction coefficient A for matching is calculated, and a preliminary correction step is performed in which the relationship α1=correction coefficient A×α2 is satisfied. Thereafter, the differential load α is calculated.

Next, a method of operating the blood component collection system 10 according to the present embodiment will be described.

The method of operating the blood component collection system 10 includes a pressure release step (see FIG. 14A) of stopping the collection and returning pump 100 at the end of the returning operation, and releasing a positive pressure inside the filter structural member 63, a clamp closure step (see FIG. 14B) of closing the inlet flow passage 63a and the outlet flow passage 63b of the filter structural member 63 by the clamps 72c and 72d, and a collection operation starting step (see FIG. 14C) of starting a subsequent collection operation by driving the collection and returning pump 100. The control unit 132 (see FIG. 1) controls the plurality of clamps 72 and the pumps 98, 100, in a manner so as to perform the pressure release step, the clamp closure step, and the collection operation starting step.

In the pressure release step, first, in order to terminate the returning operation shown in FIG. 9, as shown in FIG. 14A, the collection and returning pump 100 is stopped while the clamps 72c and 72d are opened. During execution of the returning operation by driving the collection and returning pump 100 (see FIG. 9), the collection line 42a and the returning line 42b are placed at a positive pressure. Accordingly, the interior of the filter structural member 63, which forms part of the returning line 42b, is also placed at a positive pressure. Therefore, in the case that the collection and returning pump 100 is stopped as shown in FIG. 14A, the interior of the filter structural member 63 is placed at a positive pressure at the same time that the collection and returning pump 100 is stopped.

On the other hand, since the flow path 42 of the cassette 28 is connected via the donor side tube 32 and the blood collection needle 20 to a blood vessel of the blood donor (the circuit is open), when the collection and returning pump 100 is stopped, the positive pressure of the flow path 42 is released in a comparatively short time period (on the order of 1 to 3 seconds). More specifically, after stoppage of the collection and returning pump 100, the circuit internal pressure of the cassette 28 returns to roughly 0 mmHg (or a pressure in the vicinity of 0 mmHg). Accordingly, the positive pressure of the filter structural member 63, which forms part of the returning line 42b, is released.

Next, in the clamp closure step, as shown in FIG. 14B, in the stopped state of the collection and returning pump 100, the clamps 72c and 72d are closed to thereby close the inlet flow passage 63a and the outlet flow passage 63b of the filter structural member 63, and together therewith, the clamp 72a is opened to thereby open the collection line 42a. Consequently, the plurality of clamps 72 are set to the collection mode clamping state. At this time, the internal pressure of the filter structural member 63 is approximately 0 mmHg.

As shown in FIG. 14C, in the collection operation starting step, the collection and returning pump 100 is driven to introduce blood from the blood donor into the flow path 42, and the blood is delivered to the centrifuge unit 18 (see FIG. 1) via the collection line 42a. Moreover, in the present embodiment, during each instance of the collection opera-tion, the ACC liquid transfer pump 98 is driven, and the ACD liquid together with the blood is introduced into the flow path 42.

In this case, the blood component collection system 10 according to the present embodiment and the method of operating the blood component collection system exhibit the following effects.

According to the blood component collection system 10 and the method of operating the blood component collection system 10, after the positive pressure in the filter structural member 63 is released (see FIG. 14A) by stopping the collection and returning pump 100 accompanying completion of the returning operation, the inlet flow passage 63a and the outlet flow passage 63b of the filter structural member 63 are closed (see FIG. 14B). Therefore, the subsequent collection operation is started (see FIG. 14C) in a state with the differential pressure between the collection line 42a and the returning line 42b removed. Accordingly, when the clamps 72c, 72d of the inlet flow passage 63a and the outlet flow passage 63b of the filter structural member 63 are opened for the purpose of the next returning operation, it is possible to prevent blood having a high blood cell concentration from flowing into the collection line 42a. Consequently, it is possible to prevent a decrease in the processing efficiency of the centrifugal separation device 14, together with preventing blood having a high blood cell concentration from being returned to the blood donor.

The filter accommodating unit 71 is made of a soft material. In the case that the filter accommodating unit 71 is made of a soft material, when the inlet flow passage 63a and the outlet flow passage 63b of the filter structural member 63 are closed by the clamps 72c, 72d simultaneously with completion of the returning operation, since the interior of the filter structural member 63 is maintained at a positive pressure, a rapid flow from the filter structural member 63 toward the collection line 42a easily occurs when the clamps 72c, 72d are opened to transition to the subsequent collection operation. Accordingly, the present invention is particularly useful in that, in the case that the filter accommodating unit 71 is made of a soft material, it is possible to effectively prevent a rapid flow from the filter structural member 63 toward the collection line 42a.

As shown in FIG. 2, the blood component collection device 27 is in the form of a plate-shaped cassette 28 in which the collection line 42a and the returning line 42b are formed. In accordance with such a configuration, simply by attaching the cassette 28 to the centrifugal separation device 14, the collection line 42a and the returning line 42b are arranged at predetermined positions of the centrifugal separation device 14. Accordingly, it is possible to set up the blood component collection system 10 simply and efficiently, thereby enhancing usability.

The cassette 28 includes the first common line 49 connected to the first end portion 42a1 of the collection line 42a and the first end portion 42b1 of the returning line 42b, and the second common line 53 connected to the second end portion 42a2 of the collection line 42a and the second end portion 42b2 of the returning line 42b. Consequently, since the number of ports provided in the cassette 28 can be reduced, the structure of the cassette 28 can be simplified.

The cassette 28 includes the cassette body 40 which is made of a soft material. By such a configuration, compared to a conventional cassette made of a hard resin the entirety of which is manufactured by injection molding, the cassette 28 can be manufactured at low cost.

The cassette 28 is equipped with the first pressed soft portion 60, which is pressed by the first load detecting unit 89 in an attached state of being attached to the centrifugal separation device 14, and at least the first pressed soft portion 60 is made of a soft material. Therefore, the circuit internal pressure can be measured on the basis of the load detected by the first load detecting unit 88 of the centrifugal separation device 14.

Incidentally, since the first pressed soft portion 60 is a portion forming a flow path at a location where the flow path width is comparatively narrow, even if the first pressed soft portions 60 are designed with the same width, the flexibility of the first pressed soft portions 60 may differ slightly (there may be individual differences in flexibility) depending on the materials and manufacturing methods used among such products. Concerning this point, the cassette 28 according to the present embodiment is equipped with the second pressed soft portion 61 for acquiring the correction data for the calibration curve L that is used to calculate the circuit internal pressure, and the second pressed soft portion 61 is more easily deformable than the first pressed soft portion 60 for measuring the circuit internal pressure. Therefore, it is possible to improve the measurement accuracy of the circuit internal pressure. More specifically, since the second pressed soft portion 61 is easily deformed, the relationship between the load detected by the second load detecting unit 89 and the pressure corresponding to the load is extremely stable (individual differences are small). Accordingly, by using the second load detecting unit 89 as a reference sensor for the first load detecting unit 88, and thereby correcting the slope of the calibration curve L used when calculating the circuit internal pressure, it is possible to measure the circuit internal pressure with high accuracy.

With the cassette 28 according to the present embodiment, the width W2 of the second pressed soft portion 61 is greater than the width W1 of the first pressed soft portion 60, whereby the second pressed soft portion 61 is more easily deformable than the first pressed soft portion 60. In accordance with this feature, with a simple configuration, the second pressed soft portion 61 can be more easily deformed than the first pressed soft portion 60.

In the cassette 28 according to the present embodiment, the flow path 42 is provided in the sheet-shaped cassette body 40 which is made of a soft material. In accordance with such a configuration, compared to a conventional cassette made of a hard resin and manufactured by injection molding, the cassette can be manufactured at low cost. Accordingly, with a simple and economical configuration, it is possible to measure the circuit internal pressure of the cassette 28.

The cassette 28 according to the present embodiment is equipped with the collection line forming member 54 forming the collection line 42a, and the returning line forming member 64 forming the returning line 42b, while in addition, the first pressed soft portion 60 is provided in the collection line forming member 54, and the second pressed soft portion 61 is provided in the returning line forming member 64. In this manner, since the first pressed soft portion 60 and the second pressed soft portion 61 are provided in separate lines, a simple structure is enabled by which the second pressed soft portion 61 is more easily deformable than the first pressed soft portion 60.

The second pressed soft portion 61 is made up from the filter accommodating unit 71 in which the filter member 70 is accommodated. In accordance with such a configuration, since the second pressed soft portion 61 serves both the function of the filter accommodating unit 71, and a function as a pressed portion for load detection, a rationalized structure can be achieved.

In accordance with the blood component collection system 10, the circuit internal pressure (negative pressure and positive pressure) can be accurately measured on the basis of the load detected by the first load detecting unit 88 (see FIG. 4) and the load detected by the third load detecting unit 90 (see FIG. 4) of the centrifugal separation device 14. The circuit internal pressure is calculated by the computation unit 103 (see FIG. 1) of the centrifugal separation device 14. The measured circuit internal pressure, for example, ranges from −300 to 500 mmHg.

Figure 15A:
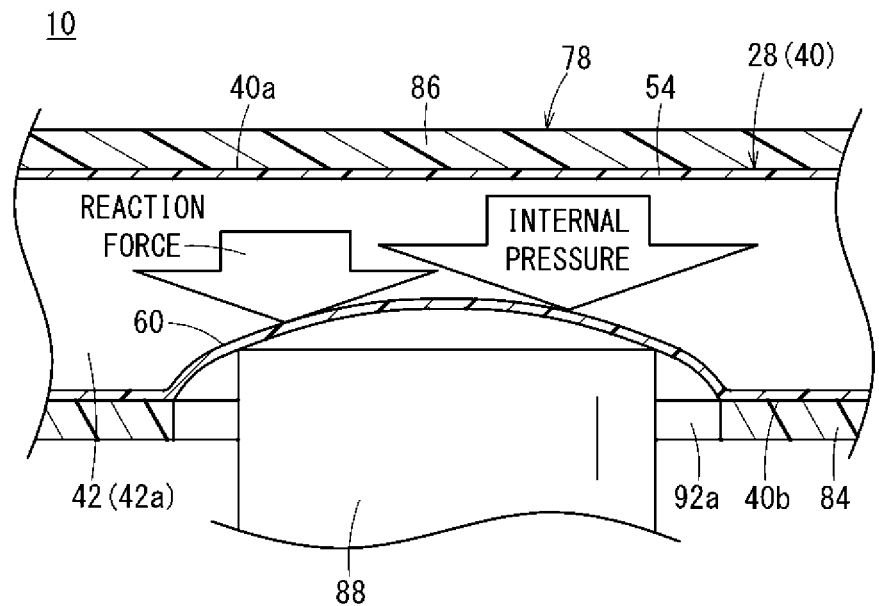
FIG. 15A is a view for explaining the detection of loads at a positive pressure.
Figure 15B:
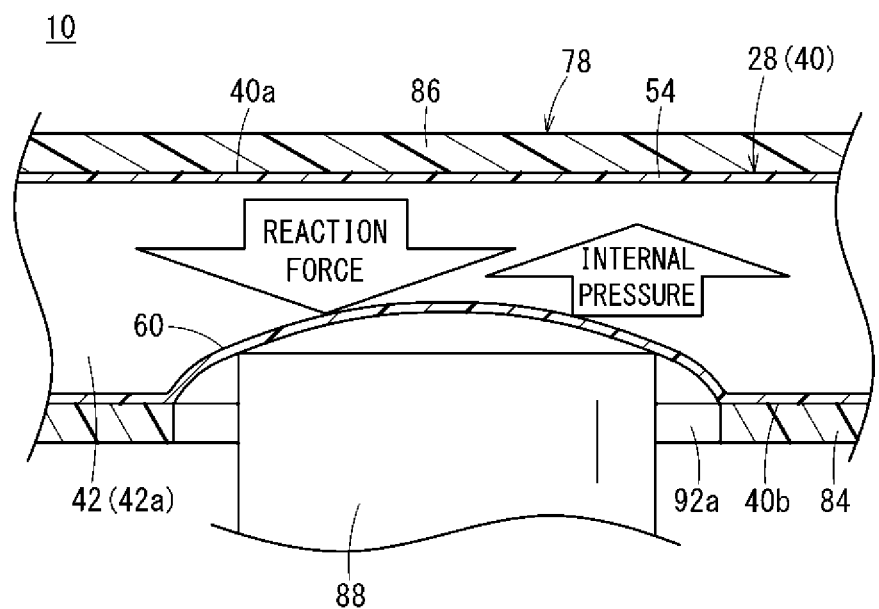
FIG. 15B is a view for explaining the detection of loads at a negative pressure.

More specifically, a load, which is obtained by summing the internal pressure (circuit internal pressure) of the collection line 42a through which the blood flows, and the reaction force of the first pressed soft portion 60 (the restorative force accompanying deformation of the first pressed soft portion 60), is detected by the first load detecting unit 88. That is, in the case that the circuit internal pressure is a positive pressure, as shown in FIG. 15A, the load that acts on the first load detecting unit 88 (the pressing force from the first pressed soft portion 60) is obtained simply by adding the circuit pressure and the reaction force. On the other hand, in the case that the circuit internal pressure is a negative pressure, as shown in FIG. 15B, the load that acts on the first load detecting unit 88 is obtained simply by subtracting the absolute value of the circuit pressure from the reaction force.

In the blood component collection system 10, the load due to the reaction force of the third pressed soft portion 62 is detected by the third load detecting unit 90. Since the hollow portion 42c is closed in a state of normal pressure, the internal pressure of the hollow portion 42c is always 0 mm Hg. Therefore, the load detected by the third load detecting unit 90 is only the reaction force of the third pressed soft portion 62 (the restorative force accompanying deformation of the third pressed soft portion 62). In addition, the reaction force of the third pressed soft portion 62 acting on the third load detecting unit 90 is the same as the reaction force of the first pressed soft portion 60 acting on the first load detecting unit 88 when the above-described preliminary correction step is performed. Therefore, by subtracting the load detected by the third load detecting unit 90 from the load detected by the first load detecting unit 88, the load due to the internal pressure of the collection line 42a through which the blood flows can be obtained. Accordingly, the circuit internal pressure can be calculated based on the load due to the internal pressure of the collection line 42a. In this case, the control unit 102 of the centrifugal separation device 14 has stored therein the calibration curve L (calibration curve data) (see FIG. 13) indicating the relationship between the load and the circuit internal pressure, and using the obtained load and the calibration curve data, it is possible to calculate the circuit internal pressure. In this case, according to the present embodiment, the corrected calibration curve La is used.

Figure 16:
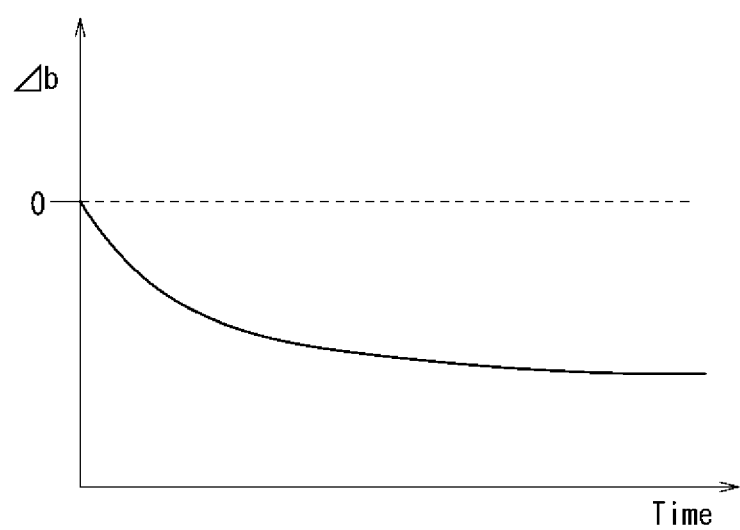
FIG. 16 is a diagram for explaining a decrease in a reaction force occurring over time.

As shown in FIG. 16, the reaction force of the first pressed soft portion 60 decreases over time. In FIG. 16, there is shown an image of a temporal change (Δb) of the reaction force of the first pressed soft portion 60 in the case that the initial reaction force is 0. The reason that the reaction force of the first pressed soft portion 60 decreases over time in the foregoing manner is due to the fact that creep is generated accompanying continuation of a state in which the first pressed soft portion 60 is pressed by the first load detecting unit 88. Accordingly, when a fixed value that does not change over time is used as the reaction force of the first pressed soft portion 60, the measurement accuracy of the circuit internal pressure is lowered.

Thus, in the blood component collection system 10, the load due to the reaction force of the third pressed soft portion 62, which decreases over time in the same manner as the reaction force of the first pressed soft portion 60, is detected in real time and used to calculate the circuit internal pressure. Consequently, it is possible to eliminate measurement errors due to a decrease in the reaction force over time, and to suppress a decrease in the measurement accuracy of the circuit internal pressure. Stated otherwise, due to the fact that the reaction force of the first pressed soft portion 60 corresponds to a segment of the function representing the above-described calibration curve L, according to the present invention, the segment of the calibration curve L is corrected in real time using the load detected by the third load detecting unit 90 (the reaction force of the third pressed soft portion 62), and thereby it is possible to eliminate measurement errors due to a decrease in the reaction force over time.

Since the reaction force is relatively large in a low pressure region as compared with a high pressure region, the adverse influence on the measurement error tends to be larger. In contrast thereto, in accordance with the present invention, the reaction force which changes over time is detected in real time, and by using the same, it is possible to eliminate measurement errors and accurately measure the circuit internal pressure.

Further, in the cassette 28, the collection line 42a and the hollow portion 42c communicate with each other in a natural state in which the cassette body 40 is not elastically deformed. In addition, the centrifugal separation device 14 is equipped with the clamp 72b which is capable of pressing the cassette body 40 so as to close the flow path 42 between the collection line 42a and the hollow portion 42c. In accordance with such a configuration, in a manufacturing process of the cassette body 40, the collection line 42a and the hollow portion 42c are capable of being formed simultaneously by blow molding. Stated otherwise, it is possible to easily form the hollow portion 42c in the cassette body 40. Further, when the centrifugal separation device 14 is in operation, by pressing a predetermined location of the cassette body 40 with the clamp 72b, it is possible to reliably and easily prevent blood from flowing into the hollow portion 42c.

A portion for trapping clotted blood (the filter member 70) is provided inside the cassette body 40. Consequently, the number of operations performed by the operator (a process to attach the filter member 70) is reduced, and usability is enhanced.

In the above-described cassette 28, the flow path 42 is formed between the first sheet 40a and the second sheet 40b, which are formed of a soft material, however, the structure that forms the flow path 42 is not necessarily limited to such a configuration. For example, within the cassette body 40, the members that form the flow path 42 may be tubes. In this case, the cassette body 40 is equipped with a first tube (the collection line forming member) having a flow path constituting the collection line 42a, a second tube (the returning line forming member) having a flow path constituting the returning line 42b, and a third tube constituting the hollow portion 42c, together with a plate-shaped cassette base portion supporting the first tube, the second tube, and the third tube.

The first pressed soft portion 60 and the clamp action member 76a are provided in the first tube. The second pressed soft portion 61 and the clamp action members 76c, 76d are provided in the second tube. The third pressed soft portion 62 and the clamp action member 76b are provided in the third tube. The cassette base portion is formed in a manner so that the first pressed soft portion 60 and the third pressed soft portion 62 are exposed, so that the first load detecting unit 88 can press the first pressed soft portion 60, and the third load detecting unit 90 can press the third pressed soft portion 62. Further, the cassette base portion is formed with the clamp action members 76a to 76d being exposed, in a manner so that the clamps 72a to 72d can press the clamp action members 76a to 76d.

Figure 17:
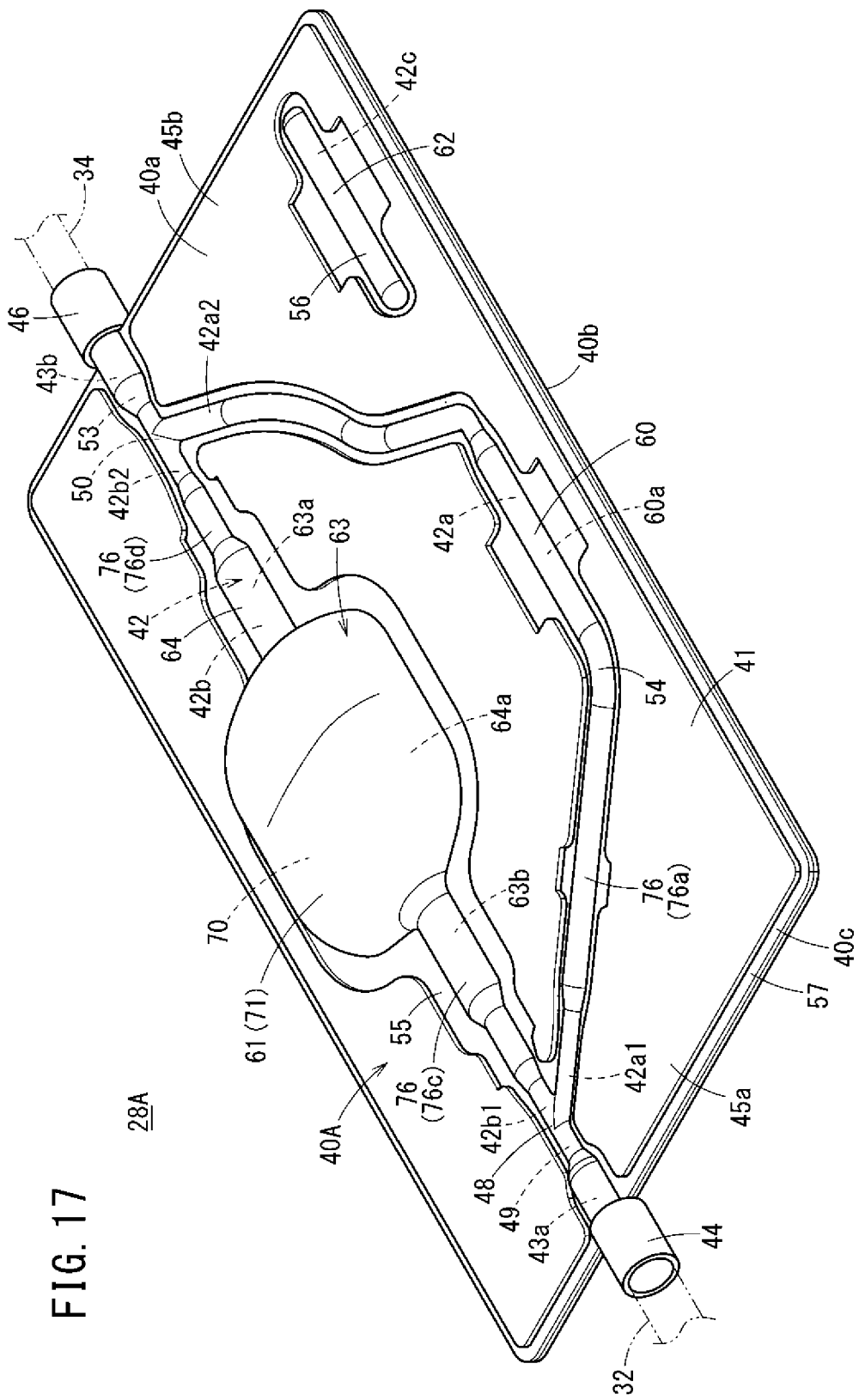
FIG. 17 is a perspective view of a cassette according to a modified example.

In the above-described blood component collection system 10, the blood component collection cassette 28A shown in FIG. 17 may be adopted instead of the cassette 28. In the cassette body 40A of the cassette 28A, the hollow portion 42c is a flow path which is independent of the collection line 42a and is not in fluid communication therewith. Accordingly, the hollow portion 42c is a space that is independent of the collection line 42a at all times, and air is enclosed in the interior thereof. The configuration of other parts of the cassette 28A is the same as that of the cassette 28 shown in FIG. 2, etc. In accordance with the cassette 28A, the clamp 72b (see FIG. 4) in the centrifugal separation device 14 can be rendered unnecessary. Therefore, the configuration of the centrifugal separation device 14 can be simplified, together with simplifying the controls related to the operation of the clamps 72.

The biological component collection device 27 is not limited to being in the form of the cassette 28 or 28A. Accordingly, the biological component collection device 27 may be equipped with a first soft tube member having the collection line 42a, and a second soft tube member having the returning line 42b, and may be constituted in a manner so that both end portions of the first soft tube member and the second soft tube member are connected together respectively via connectors.

The scope of application of the present invention is not limited to a blood component collection system 10, but may be applied to various systems through which a liquid is made to flow through a flow path, for example, a whole blood donation system, or a culture apparatus for various types of cells which are collected or cultured from patients or donors, or alternatively, a medicinal solution administration system, or the like. Accordingly, the liquid that flows in the biological component collection device (biological component collection system) is not limited to blood.

The present invention is not limited to the above-described embodiments, and various modifications may be adopted within a range that does not depart from the essence and gist of the present invention.

The invention claimed is:

1. A biological component collection system, comprising:
    a separation device having a centrifuge, and adapted to separate a biological component from a liquid containing at least one biological component; and
    a biological component collection device configured to be attachable to the separation device and having a flow path formed in an interior thereof;
    wherein the biological component collection device includes a collection line adapted to introduce the liquid containing the at least one biological component from a donor, a returning line adapted to return an uncollected biological component to the donor, and a filter structural member provided in the returning line, the collection line and the returning line communicating with each other via a branching member;
    the separation device includes a collection and returning pump disposed in a line between the centrifuge and the biological component collection device, and a clamp capable of opening and closing an inlet flow path and an outlet flow path of the filter structural member, and wherein a controller that controls the separation device drives the collection and returning pump to alternately carry out a collection operation of transferring the liquid containing the at least one biological component from the donor to the centrifuge via the collection line, and a returning operation for transferring an unnecessary biological component from the centrifuge to the donor via the returning line; and wherein the controller performs:

a pressure release step of stopping the collection and returning pump at an end of the returning operation, and releasing a positive pressure inside the filter structural member;

a clamp closure step of, after the pressure release step, controlling the clamp to close an inlet flow passage and an outlet flow passage of the filter structural member; and a collection operation starting step of, after the clamp closure step, starting a subsequent collection operation by driving the collection and returning pump.

2. The biological component collection system according to claim 1, wherein:

the filter structural member includes a filter member, and a filter accommodating section in which the filter member is accommodated; and the filter accommodating section is made of a soft material.

3. The biological component collection system according to claim 1, wherein the biological component collection device is in a form of a plate-shaped cassette in which the collection line and the returning line are formed.

4. The biological component collection system according to claim 3, wherein the cassette comprises a first common line connected to a first end portion of the collection line and a first end portion of the returning line, and a second common line connected to a second end portion of the collection line and a second end portion of the returning line.

5. The biological component collection system according to claim 3, wherein the cassette comprises a cassette body made of a soft material.

6. The biological component collection system according to claim wherein the cassette comprises a cassette body made of a soft material.

7. The biological component collection system according to claim 2, wherein the biological component collection device is in a form of a plate-shaped cassette in which the collection line and the returning line are formed.

8. The biological component collection system according to claim 7, wherein the cassette comprises a first common line connected to a first end portion of the collection line and a first end portion of the returning line, and a second common line connected to a second end portion of the collection line and a second end portion of the returning line.

9. The biological component collection system according to claim 7, wherein the cassette comprises a cassette body made of a soft material.

10. The biological component collection system according to claim 8, wherein the cassette comprises a cassette body made of a soft material.

11. A method of operating a biological component collection system, the biological component collection system comprising:

a separation device having a centrifuge, and adapted to separate a biological component from a liquid containing at least one biological component; and a biological component collection device configured to be attachable to the separation device and having a flow path formed in an interior thereof;

wherein the biological component collection device includes a collection line adapted to introduce the liquid containing the at least one biological component from a donor, a returning line adapted to return an uncollected biological component to the donor, and a filter structural member provided in the returning line, the collection line and the returning line communicating with each other via a branching member;

the separation device includes a collection and returning pump disposed in a line between the centrifuge and the biological component collection device, and a clamp capable of opening and closing an inlet flow path and an outlet flow path of the filter structural member, and by driving the collection and returning pump, alternately carries out a collection operation of transferring the liquid containing the at least one biological component from the donor to the centrifuge via the collection line, and a returning operation for transferring an unnecessary biological component from the centrifuge to the donor via the returning line; and wherein the method of operating the biological component collection system includes:

a pressure release step of stopping the collection and returning pump at an end of the returning operation, and releasing a positive pressure inside the filter structural member;

a clamp closure step of, after the pressure release step, closing an inlet flow passage and an outlet flow passage of the filter structural member by the clamp; and a collection operation starting step of, after the clamp closure step, starting a subsequent collection operation by driving the collection and returning pump.

12. The method of operating a biological component collection system according to claim 11, wherein:

the filter structural member includes a filter member, and a filter accommodating section in which the filter member is accommodated; and the filter accommodating section is made of a soft material.

13. The method of operating a biological component collection system according to claim 11, wherein the biological component collection device is in a form of a plate-shaped cassette in which the collection line and the returning line are formed.

14. The method of operating a biological component collection system according to claim 13, wherein the cassette comprises a first common line connected to a first end portion of the collection line and a first end portion of the returning line, and a second common line connected to a second end portion of the collection line and a second end portion of the returning line.

15. The method of operating a biological component collection system according to claim 13, wherein the cassette comprises a cassette body made of a soft material.

16. The method of operating a biological component collection system according to claim 14, wherein the cassette comprises a cassette body made of a soft material.

17. The method of operating a biological component collection system according to claim 12, wherein the biological component collection device is in a form of a plate-shaped cassette in which the collection line and the returning line are formed.

18. The method of operating a biological component collection system according to claim 17, wherein the cassette comprises a first common line connected to a first end portion of the collection line and a first end portion of the returning line, and a second common line connected to a second end portion of the collection line and a second end portion of the returning line.

19. The method of operating a biological component collection system according to claim 18, wherein the cassette comprises a cassette body made of a soft material.

20. The method of operating a biological component collection system according to claim 17, wherein the cassette comprises a cassette body made of a soft material.

* * * * *